(12) United States Patent
Bergmann et al.

(10) Patent No.: US 11,136,294 B2
(45) Date of Patent: Oct. 5, 2021

(54) ORGANIC MOLECULES FOR USE IN OPTOELECTRONIC DEVICES

(71) Applicant: CYNORA GMBH, Bruchsal (DE)

(72) Inventors: Larissa Bergmann, Karlsruhe (DE); Michael Danz, Eggenstein-Leopoldshafen (DE); Daniel Zink, Bruchsal (DE)

(73) Assignee: CYNORA GmbH, Bruchsal (DE)

( * ) Notice: Subject to any disclaimer, the term of this patent is extended or adjusted under 35 U.S.C. 154(b) by 387 days.

(21) Appl. No.: 16/313,103

(22) PCT Filed: Jun. 21, 2017

(86) PCT No.: PCT/EP2017/065224
§ 371 (c)(1),
(2) Date: Dec. 24, 2018

(87) PCT Pub. No.: WO2018/001820
PCT Pub. Date: Jan. 4, 2018

(65) Prior Publication Data
US 2019/0194130 A1  Jun. 27, 2019

(30) Foreign Application Priority Data

Jul. 1, 2016 (DE) ...................... 10 2016 112 077.4

(51) Int. Cl.
*C07D 209/86* (2006.01)
*C09K 11/06* (2006.01)
(Continued)

(52) U.S. Cl.
CPC .......... *C07D 209/86* (2013.01); *H01L 51/001* (2013.01); *H01L 51/0072* (2013.01); *H01L 51/5012* (2013.01)

(58) Field of Classification Search
CPC .................................................. C07D 209/86
See application file for complete search history.

(56) References Cited

U.S. PATENT DOCUMENTS

| 10,131,632 | B2* | 11/2018 | Lee | ...................... H01L 51/5016 |
| 2017/0186973 | A1* | 6/2017 | Ren | ...................... C07D 209/86 |
| 2017/0186974 | A1* | 6/2017 | Jung | ...................... H01L 51/0071 |

FOREIGN PATENT DOCUMENTS

| CN | 105418486 A | 3/2016 |
| CN | 106966955 A * | 7/2017 |

(Continued)

OTHER PUBLICATIONS

Computer-generated English-language translation of CN-106966955-A.*
SciFinder Search (Mar. 19, 2021).*

*Primary Examiner* — Vu A Nguyen
(74) *Attorney, Agent, or Firm* — Ryan, Mason & Lewis, LLP

(57) ABSTRACT

An organic molecule for use in optoelectronic components is disclosed having a structure of Formula I

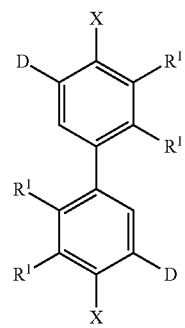

Formula I with
X=CN or $CF_3$, (Continued)

D=

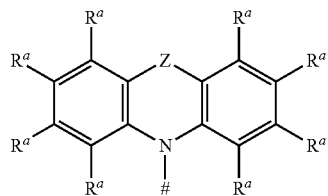

wherein
# is the point of attachment of unit D to the central biphenyl in the structure according to Formula I;
Z is a direct bond or is selected from the group consisting of $CR^3R^4$, $C=CR^3R^4$, $C=O$, $C=NR^3$, $NR^3$, $O$, $SiR^3R^4$, $S$, $S(O)$, $S(O)_2$;
In each occurrence $R^1$ is the same or different, is H, deuterium, a linear alkyl group having 1 to 5 C atoms, a linear alkenyl or alkynyl group having 2 to 8 C atoms, a branched or cyclic alkyl, alkenyl or alkynyl group having 3 to 10 C atoms, wherein one or more H atoms can be replaced by deuterium or an aromatic having 5 to 15 aromatic ring atoms, which can in each case be substituted with one or more radicals $R^6$;
and wherein at least one $R^a$ is not H.

20 Claims, 3 Drawing Sheets

(51) Int. Cl.
*H01L 51/00* (2006.01)
*H01L 51/50* (2006.01)

(56) References Cited

FOREIGN PATENT DOCUMENTS

| WO | 2015199303 A1 | 12/2015 |
| WO | 2016178463 A1 | 11/2016 |
| WO | PCT/EP2017/065224 | 8/2017 |

* cited by examiner

ORGANIC MOLECULES FOR USE IN OPTOELECTRONIC DEVICES

CROSS-REFERENCE TO RELATED APPLICATIONS

This application claims priority under 35 U.S.C. § 371 to International Application No. PCT/EP2017/065224, filed Jun. 21, 2017 which claims the benefit of DE 10 2016 112 077.4 filed Jul. 1, 2016, and entitled "ORGANIC MOLECULES, IN PARTICULAR FOR USE IN OPTOELECTRONIC DEVICES", the disclosures of which are incorporated by reference herein in their entireties.

FIELD OF INVENTION

The invention relates to purely organic molecules and the use thereof in organic light-emitting diodes (OLEDs) and in other organic optoelectronic devices.

BRIEF DESCRIPTION OF THE DRAWINGS

Exemplary embodiments of the present invention will be described below in more detail, with reference to the accompanying drawings, of which.

DESCRIPTION

Figure 1:
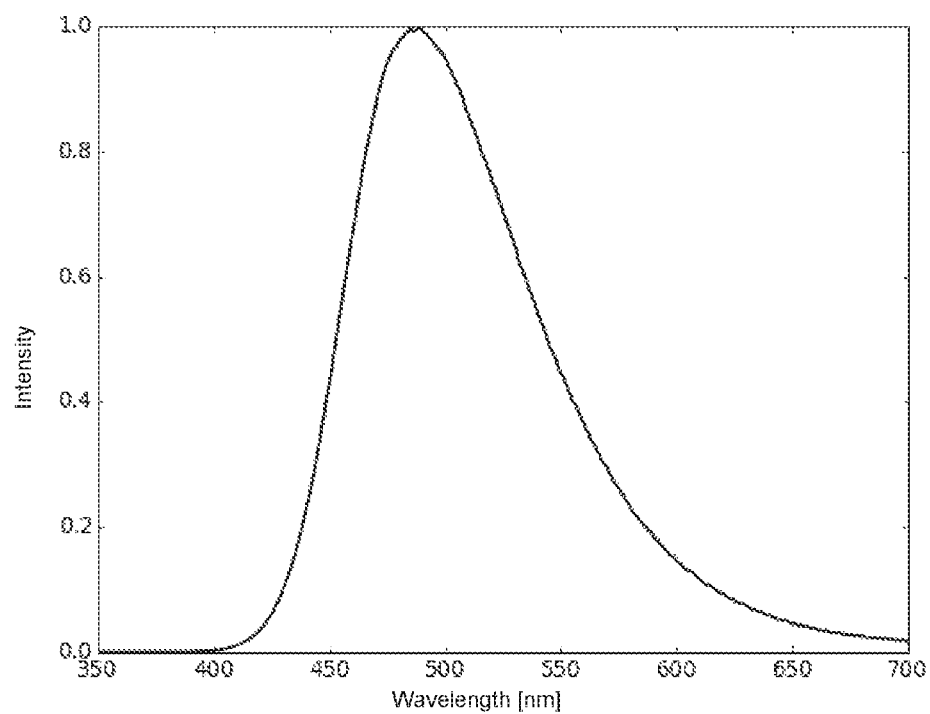
FIG. 1 is an Emission spectrum of Example 1 in 10% PMMA.

The underlying task of the present invention was to provide molecules which are suitable for use in optoelectronic devices.

DETAILED DESCRIPTION OF EXEMPLARY EMBODIMENTS OF THE INVENTION

Exemplary embodiments of the invention will now be discussed in further detail. This invention may, however, be embodied in many different forms and should not be construed as limited to the embodiments set forth herein.

The invention provides a new class of organic molecules, which are suitable for use in organic optoelectronic devices.

The organic molecules according to the invention are purely organic molecules; i.e. they do not comprise any metal ions, and thus differ from the metal complex compounds known for use in organic optoelectronic devices.

The organic molecules according to the invention are characterized by emissions in the blue, sky blue, or green spectral range. The photoluminescence quantum yields of the organic molecules according to the invention are in particular 20% and more. The molecules according to the invention in particular exhibit thermally activated delayed fluorescence (TADF). The use of the molecules according to the invention in an optoelectronic device, for example an organic light-emitting diode (OLED), results in higher efficiencies of the device. Corresponding OLEDs have a higher stability than OLEDs having known emitter materials and comparable color.

The blue spectral range here is understood to be the visible range from 430 nm to 470 nm. The sky blue spectral range here is understood to be the range between 470 nm and 499 nm. The green spectral range here is understood to be the range between 500 nm and 599 nm. The emission maximum is in the respective range.

The organic molecules have a structure of Formula I or consist of a structure according to Formula I:

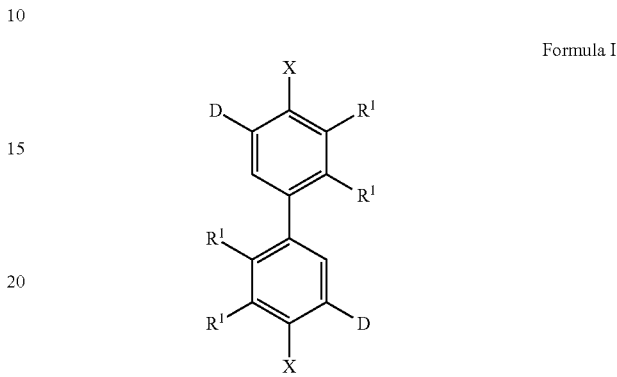

Formula I with
X=CN or $CF_3$,
D=

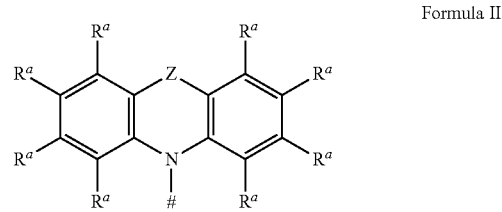

Formula II # is the point of attachment of unit D to one of the phenyl rings shown in Formula I.

Z is a direct bond or is selected from the group consisting of $CR^3R^4$, $C=CR^3R^4$, $C=O$, $C=NR^3$, $NR^3$, O, $SiR^3R^4$, S, S(O), $S(O)_2$.

In each occurrence $R^1$ is the same or different, is H, deuterium, a linear alkyl group having 1 to 5 C atoms, a linear alkenyl or alkynyl group having 2 to 8 C atoms, a branched or cyclic alkyl, alkenyl or alkynyl group having 3 to 10 C atoms, wherein one or more H atoms can be replaced by deuterium or an aromatic having 5 to 15 aromatic ring atoms, which in each case can be substituted with one or more radicals $R^6$.

In each occurrence $R^1$, $R^3$ and $R^4$ is the same or different, is H, deuterium, $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 C atoms or a linear alkenyl or alkynyl group having 2 to 40 C atoms or a branched or cyclic alkyl, alkenyl, alkynyl, alkoxy or thioalkoxy group having 3 to 40 C atoms, which can in each case be substituted with one or more radicals $R^5$, wherein one or more non-adjacent $CH_2$ groups can be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)$ $(R^5)$, SO, $SO_2$, $NR^5$, O, S or $CONR^5$ and wherein one or more H atoms can be substituted with deuterium, CN, $CF_3$ or $NO_2$; or an aromatic or heteroaromatic ring system having 5 to 60 aromatic ring atoms, which can in each case be substituted with one or more radicals $R^5$, or an aryloxy or heteroaryloxy group having 5 to 60 aromatic ring atoms, which can be substituted with one or more radicals $R^5$, or a diarylamino group, diheteroarylamino group or arylheteroarylamino group having 10 to 40 aromatic ring atoms, which can be substituted with one or more radicals $R^5$.

In each occurrence $R^5$ is the same or different, is H, deuterium, $N(R^6)_2$, OH, $Si(R^6)_3$, $B(OR^6)_2$, $OSO_2R^6$, $CF_3$, CN, F, Br, I, a linear alkyl, alkoxy or thioalkoxy group having 1 to 40 C atoms or a linear alkenyl or alkynyl group having 2 to 40 C atoms or a branched or cyclic alkyl, alkenyl, alkynyl, alkoxy or thioalkoxy group having 3 to 40 C atoms, which can in each case be substituted with one or more radicals $R^6$, wherein one or more non-adjacent $CH_2$ groups can be replaced by $R^6C=CR^6$, $C≡C$, $Si(R^6)_2$, $Ge(R^6)_2$, $Sn(R^6)_2$, C=O, C=S, C=Se, C=NR^6, P(=O)(R^6), SO, SO_2, NR^6, O, S$ or $CONR^6$ and wherein one or more H atoms can be substituted with deuterium, CN, $CF_3$ or $NO_2$; or an aromatic or heteroaromatic ring system having 5 to 60 aromatic ring atoms, which can in each case be substituted with one or more radicals $R^6$, or an aryloxy or heteroaryloxy group having 5 to 60 aromatic ring atoms, which can be substituted with one or more radicals $R^6$, or a diarylamino group, diheteroarylamino group or arylheteroarylamino group having 10 to 40 aromatic ring atoms, which can be substituted with one or more radicals $R^6$.

In each occurrence $R^6$ is the same or different, is H, deuterium, OH, $CF_3$, CN, F, Br, I, a linear alkyl, alkoxy or thioalkoxy group having 1 to 5 C atoms or a linear alkenyl or alkynyl group having 2 to 5 C atoms or a branched or cyclic alkyl, alkenyl, alkynyl, alkoxy or thioalkoxy group having 3 to 5 C atoms, wherein one or more H atoms can be replaced by deuterium, CN, $CF_3$ or $NO_2$; or an aromatic or heteroaromatic ring system having 5 to 60 aromatic ring atoms or an aryloxy or heteroaryloxy group having 5 to 60 aromatic ring atoms or a diarylamino group, diheteroarylamino group or arylheteroarylamino group having 10 to 40 aromatic ring atoms.

Each of the radicals $R^a$, $R^3$, $R^4$ or $R^5$ can also form a mono- or polycyclic, aliphatic, aromatic and/or benzoannelated ring system with one or more further radicals $R^a$, $R^3$, $R^4$ or $R^5$.

According to the invention, at least one $R^a$ is not H.

In one embodiment of the organic molecules, $R^1$ is H or methyl.

In a further embodiment, both X are CN.

In one embodiment of the organic molecules, the two Groups D are identical; in another embodiment, the two Groups D are different.

In another embodiment of the organic molecules, one Group D or both Groups D comprise or consist of a structure of Formula IIa or consist(s) of a structure of Formula IIa:

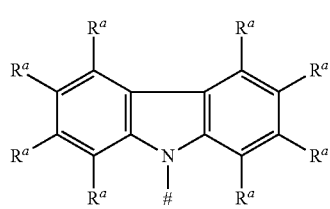

Formula IIa wherein the abovementioned definitions apply for # and $R^a$.

In another embodiment of the organic molecules according to the invention, Group D comprises or both Groups D comprise a structure of Formula IIb, Formula IIb-2 or Formula IIb-3 or consist(s) thereof:

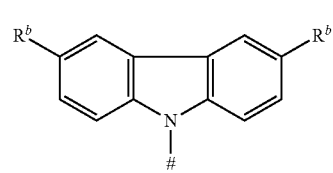

Formula IIb

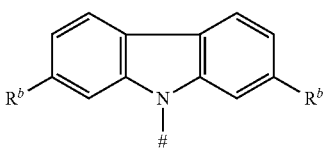

Formula IIb-2

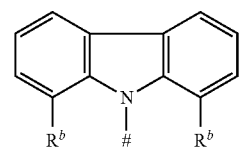

Formula IIb-3 wherein
In each occurrence $R^b$ is the same or different, is $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 C atoms or a linear alkenyl or alkynyl group having 2 to 40 C atoms or a branched or cyclic alkyl, alkenyl, alkynyl, alkoxy or thioalkoxy group having 3 to 40 C atoms, which in each case can be substituted with one or more radicals $R^5$, wherein one or more non-adjacent $CH_2$ groups can be replaced by $R^5C=CR^5$, $C≡C$, $Si(R^5)_2$, $Ge(R^5)_2$, $Sn(R^5)_2$, C=O, C=S, C=Se, C=NR^5, P(=O)(R^5), SO, SO_2, NR^5, O, S$ or $CONR^5$ and wherein one or more H atoms can be substituted with deuterium, CN, $CF_3$ or $NO_2$; or an aromatic or heteroaromatic ring system having 5 to 60 aromatic ring atoms, which can be substituted with one or more radicals $R^5$, or an aryloxy or heteroaryloxy group having 5 to 60 aromatic ring atoms, which can be substituted with one or more radicals $R^5$, or a diarylamino group, diheteroarylamino group or arylheteroarylamino group having 10 to 40 aromatic ring atoms, which can be substituted with one or more radicals $R^5$.

Otherwise, the above-mentioned definitions apply.

In another embodiment of the organic molecules according to the invention, Group D has or both Groups D have a structure of Formula IIc, Formula IIc-2 or Formula IIc-3 or consist(s) thereof:

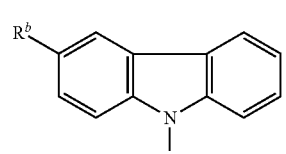

Formula IIc

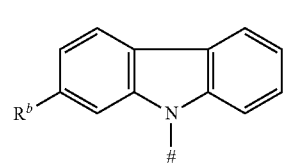

Formula IIc-2

Formula IIc-3

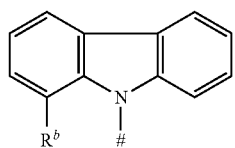

wherein the abovementioned definitions apply.

In a further embodiment of the organic molecules according to the invention, in each occurrence $R^b$ is independently selected from the group consisting of Me, $^i$Pr, $^t$Bu, CN, CF$_3$, Ph, which can in each case be substituted with one or more radicals selected from Me, $^i$Pr, $^t$Bu, CN, CF$_3$ or Ph, pyridinyl, pyrimidinyl, carbazolyl, which in each case can be substituted with one or more radicals selected from Me, $^i$Pr, $^t$Bu, CN, CF$_3$, or Ph, and N(Ph)$_2$.

Embodiments of Group D are shown in the following as examples:

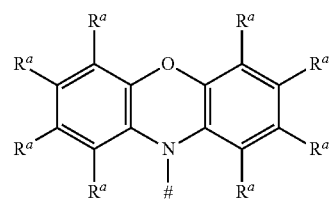

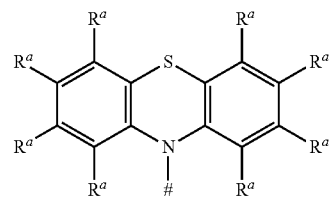

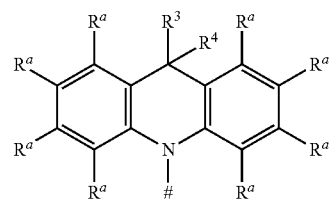

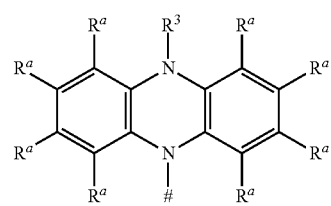

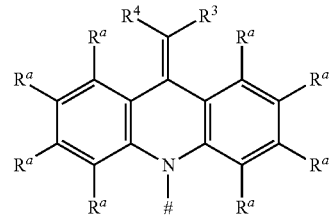

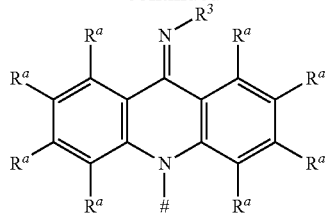

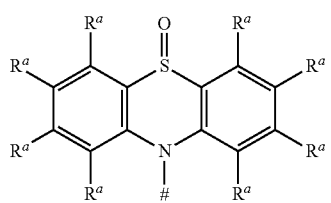

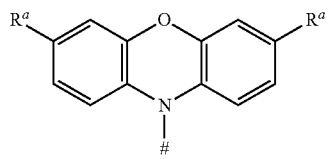

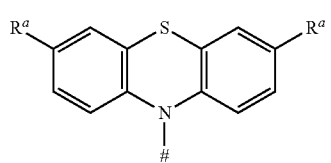

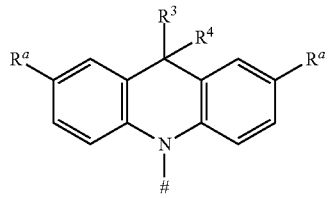

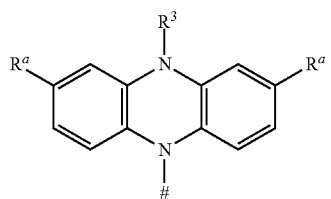

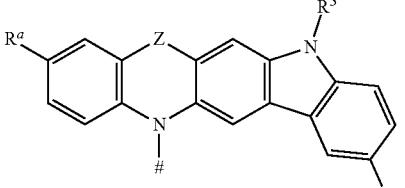

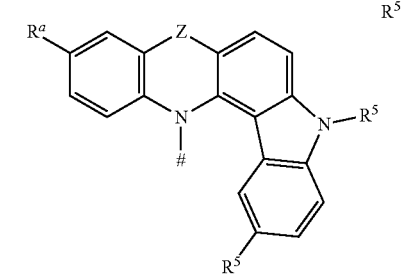

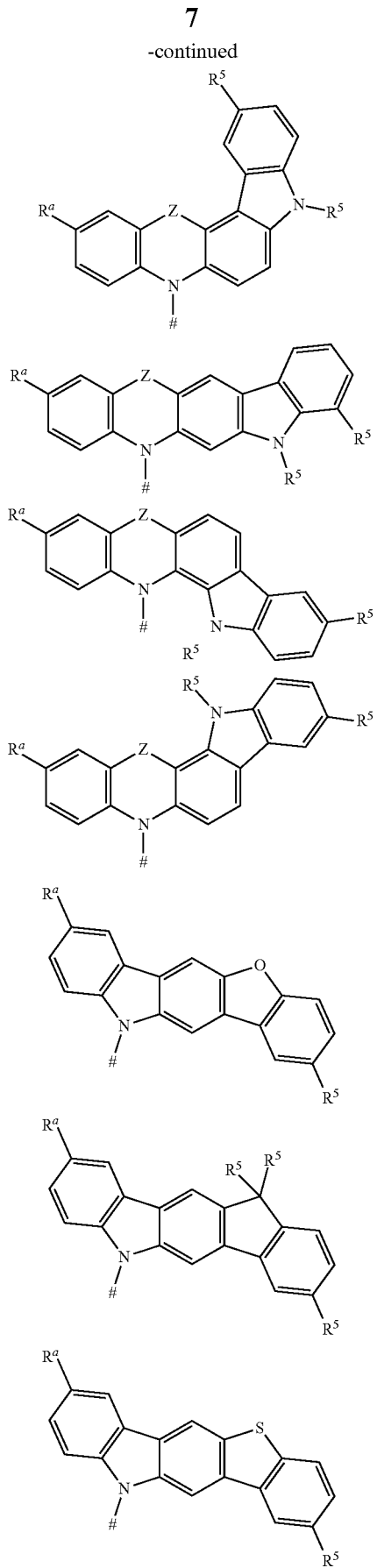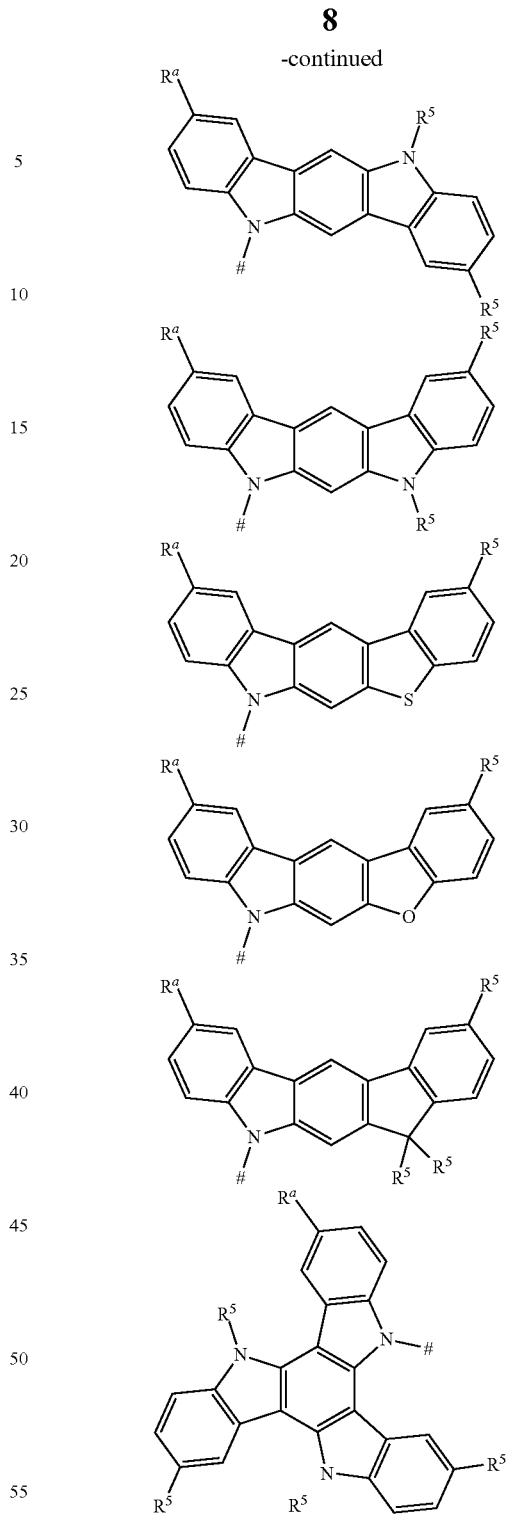

wherein the abovementioned definitions apply for #, $R^a$ and $R^5$. In one embodiment, in each occurrence, the radical $R^5$ is the same or different and is selected from the group consisting of H, methyl, ethyl, phenyl and mesityl. In one embodiment, in each occurrence, the radical $R^a$ is the same or different and is selected from the group consisting of H, methyl (Me), i-propyl ($CH(CH_3)_2$) ($^iPr$), t-butyl ($^tBu$), phenyl (Ph), CN, $CF_3$ and diphenylamine ($NPh_2$).

In the context of this invention, an aryl group contains 6 to 60 aromatic ring atoms; a heteroaryl group contains 5 to 60 aromatic ring atoms, at least one of which represents a heteroatom. The heteroatoms are, in particular, N, O and/or S. In the event that other definitions, which differ from the stated definitions, for example with respect to the number of aromatic ring atoms or the contained heteroatoms, are specified in the description of specific embodiments of the invention, then these definitions apply.

An aryl group or heteroaryl group is understood to be a simple aromatic ring, i.e. benzene, or a simple heteroaromatic ring, for example pyridine, pyrimidine or thiophene, or a heteroaromatic polycyclic compound, for example phenanthrene, quinoline or carbazole. In the context of the present application, a condensed (annelated) aromatic or heteroaromatic polycyclic compound consists of two or more simple aromatic or heteroaromatic rings which are condensed with one another.

An aryl or heteroaryl group, which can in each case be substituted with the abovementioned radicals and which can be linked to the aromatic or heteroaromatic group via any desired positions, are in particular understood to be groups which are derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, isoquinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, napthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, purine, pteridine, indolizine and benzothiadiazole or combinations of said groups.

A cyclic alkyl, alkoxy or thioalkoxy group is understood here to be a monocyclic, a bicyclic or a polycyclic group.

Within the scope of the present invention, a $C_1$ to $C_{40}$ alkyl group, in which individual H atoms or $CH_2$ groups can also be substituted by the groups mentioned above, are understood to be, for example, the radicals methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2,2,2]octyl, 2-bicyclo[2,2,2]-octyl, 2-(2,6-dimethyl)octyl, 3-(3,7-dimethyl)octyl, adamantyl, trifluoromethyl, pentafluorethyl, 2,2,2-trifluorethyl, 1,1-dimethyl-n-hex-1-yl-, 1,1-dimethyl-n-hept-1-yl-, 1,1-dimethyl-n-oct-1-yl-, 1,1-dimethyl-n-dec-1-yl-, 1,1-dimethyl-n-dodec-1-yl-, 1,1-dimethyl-n-tetradec-1-yl-, 1,1-dimethyl-n-hexadec-1-yl-, 1,1-dimethyl-n-octadec-1-yl-, 1,1-diethyl-n-hex-1-yl-, 1,1-diethyl-n-hept-1-yl-, 1,1-diethyl-n-oct-1-yl-, 1,1-diethyl-n-dec-1-yl-, 1,1-diethyl-n-dodec-1-yl-, 1,1-diethyl-n-tetradec-1-yl-, 1,1-diethyl-n-hexadec-1-yl-, 1,1-diethyl-n-octadec-1-yl-, 1-(n-propyl)-cyclohex-1-yl-, 1-(n-butyl)-cyclohex-1-yl-, 1-(n-hexyl)-cyclohex-1-yl-, 1-(n-octyl)-cyclohex-1-yl- and 1-(n-decyl)-cyclohex-1-yl. An alkenyl group is understood to be ethenyl, propenyl, butenyl, pentenyl, cyclopentenyl, hexenyl, cyclohexenyl, heptenyl, cycloheptenyl, octenyl, cyclooctenyl or cyclooctadienyl, for example. An alkynyl group is understood to be ethynyl, propynyl, butynyl, pentynyl, hexynyl, heptynyl or octynyl, for example. A $C_1$ to $C_{40}$ alkoxy group is understood to be methoxy, trifluoromethoxy, ethoxy, n-propoxy, i-propoxy, n-butoxy, i-butoxy, s-butoxy, t-butoxy or 2-methylbutoxy, for example.

One embodiment of the invention relates to organic molecules, which have an $\Delta E(S_1-T_1)$ value between the lowest excited singlet ($S_1$) state and the triplet ($T_1$) state below it that is no higher than 5000 cm$^{-1}$, in particular no higher than 3000 cm$^{-1}$, or no higher than 1500 cm$^{-1}$ or 1000 cm$^{-1}$ and/or an emission lifetime of at most 150 μs, in particular at most 100 μs, at most 50 μs, or at most 10 μs and/or a main emission band having a full width at half maximum (FWHM) of less than 0.55 eV, in particular less than 0.50 eV, less than 0.48 eV, or less than 0.45 eV.

In a further aspect, the invention relates to a method for producing an organic molecule according to the invention of the type described here (with a possible subsequent reaction), wherein a in 5 and 6 position $R^1$-substituted 4-bromo-2-fluorobenzonitrile or a in 5 and 6 position $R^1$-substituted 4-bromo-2-fluorobenzotrifluoride is used as the educt.

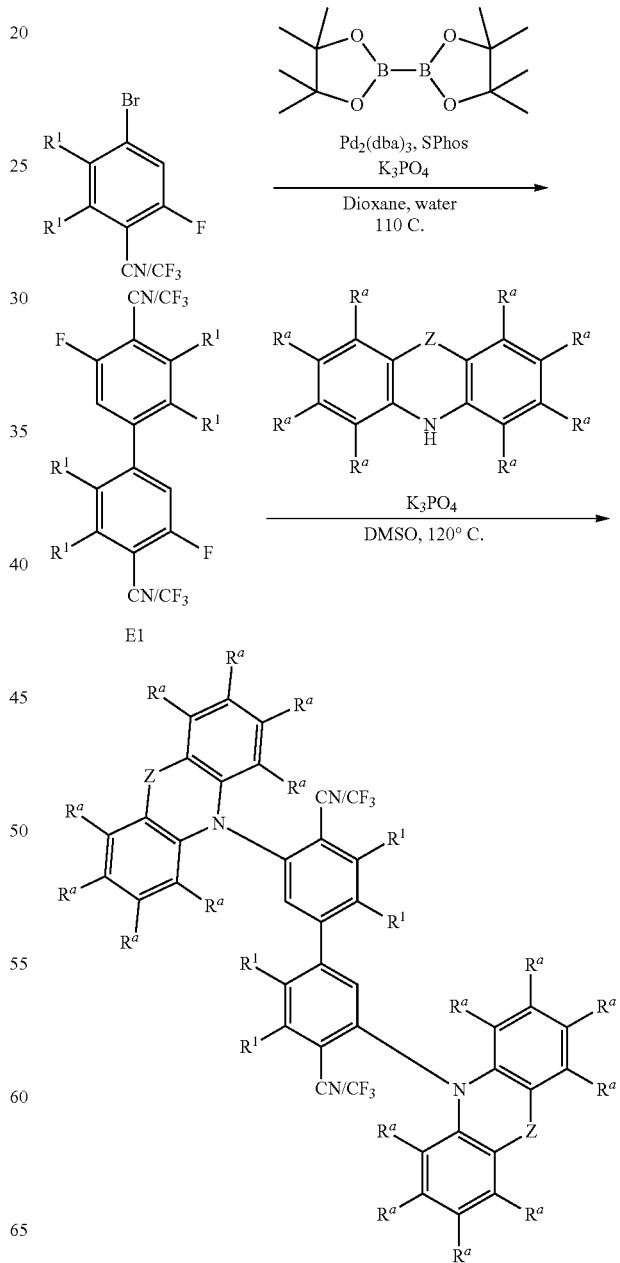

In one embodiment, the corresponding coupling reactant is produced by reacting in 5 and 6 position $R^1$-substituted 4-bromo-2-fluorobenzonitrile or in 5 and 6 position $R^1$-substituted 4-bromo-2-fluorobenzotrifluoride with bis(pinacolato)diboron (4,4,4',4',5,5,5',5'-octamethyl-2,2'-bi-1,3,2-dioxaborolane) in situ, and converted in a palladium-catalyzed cross-coupling reaction. The product is obtained by deprotonation of the corresponding amine and subsequent nucleophilic substitution of the fluorine groups. To do this, a nitrogen heterocyclic compound is reacted with an educt E1 in the context of a nucleophilic aromatic substitution. Typical conditions include the use of a base, such as potassium phosphate tribasic or sodium hydride, in an aprotic polar solvent, such as dimethyl sulfoxide (DMSO) or N,N-dimethylformamide (DMF).

In a further aspect, the invention relates to the use of the organic molecules as luminescent emitters or as host material in an organic optoelectronic device, in particular wherein the organic optoelectronic device is selected from the group consisting of:
- organic light-emitting diodes (OLEDs),
- light-emitting electrochemical cells,
- OLED sensors, in particular in gas and vapor sensors which are not hermetically shielded to the outside,
- organic diodes,
- organic solar cells,
- organic transistors,
- organic field-effect transistors,
- organic lasers and
- down-conversion elements.

In a further aspect, the invention relates to a composition comprising or consisting of:
(a) at least one organic molecule according to the invention, in particular as an emitter and/or host, and
(b) at least one, i.e. one or more emitter and/or host materials, that is or are different from the organic molecule according to the invention, and
(c) optionally one or more dyes and/or one or more organic solvents.

In one embodiment, the composition according to the invention consists of an organic molecule according to the invention and one or more host materials. In particular, the host material or materials possess triplet ($T_1$) and singlet ($S_1$) energy levels, which are energetically higher than the triplet ($T_1$) and singlet ($S_1$) energy levels of the organic molecule according to the invention. In one embodiment, in addition to the organic molecule according to the invention, the composition has an electron-dominant and a hole-dominant host material. The highest occupied orbital (HOMO) and the lowest unoccupied orbital (LUMO) of the hole-dominant host material are in particular energetically higher than that of the electron-dominant host material. The HOMO of the hole-dominant host material is energetically below the HOMO of the organic molecule according to the invention, while the LUMO of the electron-dominant host material is energetically above the LUMO of the organic molecule according to the invention. In order to avoid exciplex formation between emitter and host material or host materials, the materials should be selected such that the energy distances between the respective orbitals are small. The distance between the LUMO of the electron-dominant host material and the LUMO of the organic molecule according to the invention is in particular less than 0.5 eV, preferably less than 0.3 eV, even more preferably less than 0.2 eV. The distance between the HOMO of the hole-dominant host material and the HOMO of the organic molecule according to the invention is in particular less than 0.5 eV, preferably less than 0.3 eV, even more preferably less than 0.2 eV.

In a further aspect, the invention relates to an organic optoelectronic device which comprises an organic molecule according to the invention or a composition according to the invention. The organic optoelectronic device is in particular formed as a device selected from the group consisting of organic light-emitting diode (OLED); light-emitting electrochemical cell; OLED sensor, in particular gas and vapor sensors which are not hermetically shielded to the outside; organic diode; organic solar cell; organic transistor; organic field-effect transistor; organic laser and down-conversion element.

An organic optoelectronic device comprising
a substrate,
an anode and
a cathode, wherein the anode or the cathode are disposed on the substrate, and
at least one light-emitting layer, which is disposed between the anode and the cathode and which comprises an organic molecule according to the invention, represents a further embodiment of the invention.

In one embodiment, the optoelectronic device is an OLED. A typical OLED, for example, has the following layer structure:
1. Substrate (supporting material)
2. Anode
3. Hole injection layer (HIL)
4. Hole transport layer (HTL)
5. Electron blocking layer (EBL)
6. Emitting layer (EML)
7. Hole blocking layer (HBL)
8. Electron transport layer (ETL)
9. Electron injection layer (EIL)
10. Cathode.

The presence of specific layers is merely optional. Several of these layers can also coincide. Specific layers can also be present more than once in the component.

According to one embodiment, at least one electrode of the organic component is designed to be translucent. In this case, "translucent" describes a layer that is transmissive to visible light. The translucent layer can be clearly translucent, i.e. transparent, or at least partially light-absorbing and/or partially light-diffusing, so that the translucent layer can, for example, also be diffusely or milkily translucent. A layer referred to here as translucent is in particular designed to be as transparent as possible, so that in particular the absorption of light is as low as possible.

According to a further embodiment, the organic component, in particular an OLED, comprises an inverted structure. The inverted structure is characterized in that the cathode is located on the substrate and the other layers are disposed in a correspondingly inverted manner:
1. Substrate (supporting material)
2. Cathode
3. Electron injection layer (EIL)
4. Electron transport layer (ETL)
5. Hole blocking layer (HBL)
6. Emission layer or emitting layer (EML)
7. Electron blocking layer (EBL)
8. Hole transport layer (HTL)
9. Hole injection layer (HIL)
10. Anode The presence of specific layers is merely optional. Several of these layers can also coincide. Specific layers can also be present more than once in the component.

In one embodiment, in the inverted OLED, the anode layer of the typical structure e.g. an ITO layer (indium tin oxide), is connected as the cathode.

According to a further embodiment, the organic component, in particular an OLED, comprises a stacked structure. In doing so, the individual OLEDs are arranged one above the other and not next to one another as usual. The production of mixed light can be made possible with the aid of a stacked structure. This structure can be used to produce white light, for example. To produce said white light, the entire visible spectrum is typically imaged by combining the emitted light of blue, green and red emitters. Furthermore, with practically the same efficiency and identical luminance, significantly longer lifetimes can be achieved in comparison to conventional OLEDs. A so-called charge generation layer (CGL) between two OLEDs is optionally used for the stacked structure. Said layer consists of an n-doped and a p-doped layer, wherein the n-doped layer is typically disposed closer to the anode.

In one embodiment—a so-called tandem OLED—two or more emission layers occur between the anode and the cathode. In one embodiment, three emission layers are arranged one above the other, wherein one emission layer emits red light, one emission layer emits green light and one emission layer emits blue light, and additional charge generation, blocking or transport layers are optionally disposed between the individual emission layers. In a further embodiment, the respective emission layers are disposed directly adjacent to one another. In another embodiment, one respective charge generation layer is situated between the emission layers. Emission layers that are directly adjacent to one another and emission layers that are separated by charge generation layers can furthermore be combined in an OLED.

An encapsulation arrangement can furthermore be disposed above the electrodes and the organic layers as well. The encapsulation arrangement can, for example, be designed in the form of a glass cover or in the form of a thin-film encapsulation arrangement.

The supporting material of the optoelectronic device can, for example, be glass, quartz, plastic, metal, a silicon wafer or any other suitable solid or flexible, optionally transparent material. The supporting material can, for example, comprise one or more materials in the form of a layer, a film, a plate or a laminate.

Transparent conductive metal oxides such as, for example, ITO (indium tin oxide), zinc oxide, tin oxide, cadmium oxide, titanium oxide, indium oxide or aluminum zinc oxide (AZO), $Zn_2SnO_4$, $CdSnO_3$, $ZnSnO_3$, $MgIn_2O_4$, $GaInO_3$, $Zn_2In_2O_5$ or $In_4Sn_3O_{12}$ or mixtures of different transparent conductive oxides, for example, can be used as the anode of the optoelectronic device.

PEDOT:PSS (poly-3,4-ethylenedioxythiophene-polystyrene sulfonic acid), PEDOT (poly-3,4-ethylenedioxythiophene), m-MTDATA (4,4',4"-tris[phenyl(m-tolyl)amino]triphenylamine), Spiro-TAD (2,2',7,7'-tetrakis(N,N-diphenylamino)-9,9-spirobifluorene), DNTPD (4,4'-bis[N-[4-{N,N-bis(3-methyl-phenyl)amino}phenyl]-N-phenylamino]biphenyl), NPB (N,N'-bis-(1-naphthalenyl)-N,N'-bis-phenyl-(1,1'-biphenyl)-4,4'-diamine), NPNPB (N,N'-diphenyl-N,N'-di-[4-(N,N-diphenyl-amino)phenyl]benzene), MeO-TPD (N,N,N',N'-tetrakis(4-methoxyphenyl)benzene), HAT-CN (1,4,5,8,9,11-hexaazatriphenylene-hexacarbonitrile) or Spiro-NPD (N,N'-diphenyl-N,N'-bis-(1-naphthyl)-9,9'-spirobifluorene-2,7-diamine), for example, are suitable materials for an HIL. The layer thickness is 10-80 nm, for example. Small molecules (e.g. copper phthalocyanine (CuPc e.g. 10 nm thick)) or metal oxides, such as $MoO_3$, $V_2O_5$, can also be used.

Tertiary amines, carbazole derivatives, polyethylenedioxythiophene doped with polystyrene sulfonic acid, polyaniline poly-TPD (poly(4-butylphenyl-diphenyl-amine)) doped with camphorsulfonic acid, [alpha]-NPD (poly(4-butylphenyl-diphenyl-amine)), TAPC (4,4'-cyclohexylidene-bis[N,N-bis(4-methylphenyl)benzenamine]), TCTA (tris(4-carbazoyl-9-ylphenyl)amine), 2-TNATA (4,4',4"-tris[2-naphthyl(phenyl)amino]triphenylamine), Spiro-TAD, DNTPD, NPB, NPNPB, MeO-TPD, HAT-CN or TrisPcz (9,9'-diphenyl-6-(9-phenyl-9H-carbazole-3-yl)-9H,9'H-3,3'-bicarbazole) can be used as materials for an HTL. The layer thickness is 10 nm to 100 nm, for example.

The HTL can comprise a p-doped layer comprising an inorganic or organic dopant in an organic hole transporting matrix. Transition metal oxides such as vanadium oxide, molybdenum oxide or tungsten oxide, for example, can be used as the inorganic dopant. Tetrafluorotetracyanoquinodimethane (F4-TCNQ), copper pentafluorobenzoate (Cu(I) pFBz) or transition metal complexes can, for example, be used as the organic dopants. The layer thickness is 10 nm to 100 nm, for example.

MCP (1,3-bis(carbazole-9-yl)benzene), TCTA, 2-TNATA, mCBP (3,3-Di(9H-carbazole-9-yl)biphenyl), tris-Pcz (9,9'-diphenyl-6-(9-phenyl-9H-carbazole-3-yl)-9H,9'H-3,3'-bicarbazole), CzSi (9-(4-tert-butylphenyl)-3,6-bis(triphenylsilyl)-9H-carbazole) or DCB (N,N'-dicarbazolyl-1,4-dimethylbenzene) can, for example, be used as the materials of an electron blocking layer. The layer thickness is 10 nm to 50 nm, for example.

The emitter layer EML or emission layer consists of or contains emitter material or a mixture comprising at least two emitter materials and optionally one or more host materials. Suitable host materials are, for example, mCP, TCTA, 2-TNATA, mCBP, CBP (4,4'-bis-(N-carbazolyl)-biphenyl), Sif87 (dibenzo[b,d]thiophene-2-yltriphenylsilane), Sif88 (dibenzo[b,d]thiophene-2-yl)diphenylsilane) or DPEPO (bis[2-((oxo)diphenylphosphino)phenyl]ether). The common matrix materials, such as CBP, are suitable for emitter material emitting in the green or in the red range or for a mixture comprising at least two emitter materials. UHG matrix materials (ultra-high energy gap materials) (see, for example, M. E. Thompson et al, Chem. Mater. 2004, 16, 4743) or other so-called wide-gap matrix materials can be used for emitter material emitting in the blue range or a mixture comprising at least two emitter materials. The layer thickness is 10 nm to 250 nm, for example.

The hole blocking layer HBL can, for example, comprise BCP (2,9-dimethyl-4,7-diphenyl-1,10-phenanthroline=bathocuproine), bis-(2-methyl-8-hydroxyquinolinato)-(4-phenylphenolato)-aluminum(III) (BAlq), Nbphen (2,9-bis(naphthalene-2-yl)-4,7-diphenyl-1,10-phenanthroline), Alq3 (aluminum-tris(8-hydroxyquinoline)), TSPO1 (diphenyl-4-triphenylsilyl-phenylphosphine oxide) or TCB/TCP (1,3,5-tris(N-carbazolyl)benzene/1,3,5-tris(carbazole)-9-yl)benzene). The layer thickness is 10 nm to 50 nm, for example.

The electron transport layer ETL can, for example, comprise materials based on $AlQ_3$, TSPO1, BPyTP2 (2,7-di(2,2'-bipyridine-5-yl)triphenyl)), Sif87, Sif88, BmPyPhB (1,3-bis[3,5-di(pyridine-3-yl)phenyl]benzene) or BTB (4,4'-bis-[2-(4,6-diphenyl-1,3,5-triazinyl)]-1,1'-biphenyl). The layer thickness is 10 nm to 200 nm, for example.

CsF, LiF, 8-hydroxyquinolinolatolithium (Liq), $Li_2O$, $BaF_2$, MgO or NaF can be used as materials for a thin electron injection layer EIL.

Metals or alloys, for example Al, Al>AlF, Ag, Pt, Au, Mg, Ag:Mg, can be used as materials of the cathode layer. Typical layer thicknesses are 100 nm to 200 nm. In particular, one or more metals are used, which are stable when exposed to air and/or which are self-passivating, for example by forming a thin protective oxide layer.

Aluminum oxide, vanadium oxide, zinc oxide, zirconium oxide, titanium oxide, hafnium oxide, lanthanum oxide, tantalum oxide, for example, are suitable materials for encapsulation. The person skilled in the art is well aware of which combinations of materials can be used for an optoelectronic device comprising an organic molecule according to the invention.

In one embodiment of the organic optoelectronic device according to the invention, the organic molecule according to the invention is used as the emission material in a light-emitting layer EML, wherein it is used either as a pure layer or in combination with one or more host materials.

In another embodiment, the mass fraction of the organic molecule according to the invention in the emitter layer EML of a light-emitting layer in devices emitting optical light, in particular in OLEDs, is between 1% and 80%. In one embodiment of the organic optoelectronic device according to the invention, the light-emitting layer is disposed on a substrate, wherein an anode and a cathode are preferably disposed on the substrate and the light-emitting layer is disposed between the anode and the cathode.

The light-emitting layer can comprise only one organic molecule according to the invention in 100% concentration, wherein the anode and the cathode are disposed on the substrate, and the light-emitting layer is disposed between the anode and the cathode.

In one embodiment of the organic optoelectronic device according to the invention, a hole- and electron-injecting layer is disposed between the anode and the cathode, and a hole- and electron-transporting layer is disposed between the hole- and electron-injecting layer, and the light-emitting layer is disposed between the hole- and electron-transporting layer.

In another embodiment of the invention, the organic optoelectronic device comprises: a substrate, an anode, a cathode and at least one respective hole- and electron-injecting layer, and at least one respective hole- and electron-transporting layer, and at least one light-emitting layer, the organic molecule according to the invention and one or more host materials the triplet ($T_1$) and singlet ($S_1$) energy levels of which are energetically higher than the triplet ($T_1$) and singlet ($S_1$) energy levels of the organic molecule, wherein the anode and the cathode are disposed on the substrate, and the hole- and electron-injecting layer is disposed between the anode and the cathode, and the hole- and electron-transporting layer is disposed between the hole- and electron-injecting layer, and the light-emitting layer is disposed between the hole- and electron-transporting layer.

In a further aspect, the invention relates to a method for producing an optoelectronic component. To do this, an organic molecule according to the invention is used.

In one embodiment, the production method comprises the processing of the organic molecule according to the invention by means of a vacuum evaporation method or from a solution.

The invention also relates to a method for producing an optoelectronic device according to the invention, in which at least one layer of the optoelectronic device
  is coated using a sublimation process,
  is coated using an OVPD (organic vapor phase deposition) process,
  is coated using a carrier-gas sublimation, and/or
  is produced from solution or using a pressure process.

Known methods are used for the production of the optoelectronic device according to the invention. The layers are generally disposed individually onto a suitable substrate in successive deposition method steps. The common methods, such as thermal evaporation, chemical vapor deposition (CVD), physical vapor deposition (PVD) can be used for the vapor deposition. For active matrix OLED (AMOLED) displays, deposition takes place onto an AMOLED backplane as the substrate.

Layers can alternatively be deposited from solutions or dispersions in suitable solvents. Spin coating, dip coating and jet pressure methods are examples of suitable coating methods. According to the invention, the individual layers can be produced via the same as well as via respective different coating methods.

The invention will now be explained in more detail using the following examples without the intent to thereby restrict said invention.

EXAMPLES

General Synthesis Scheme

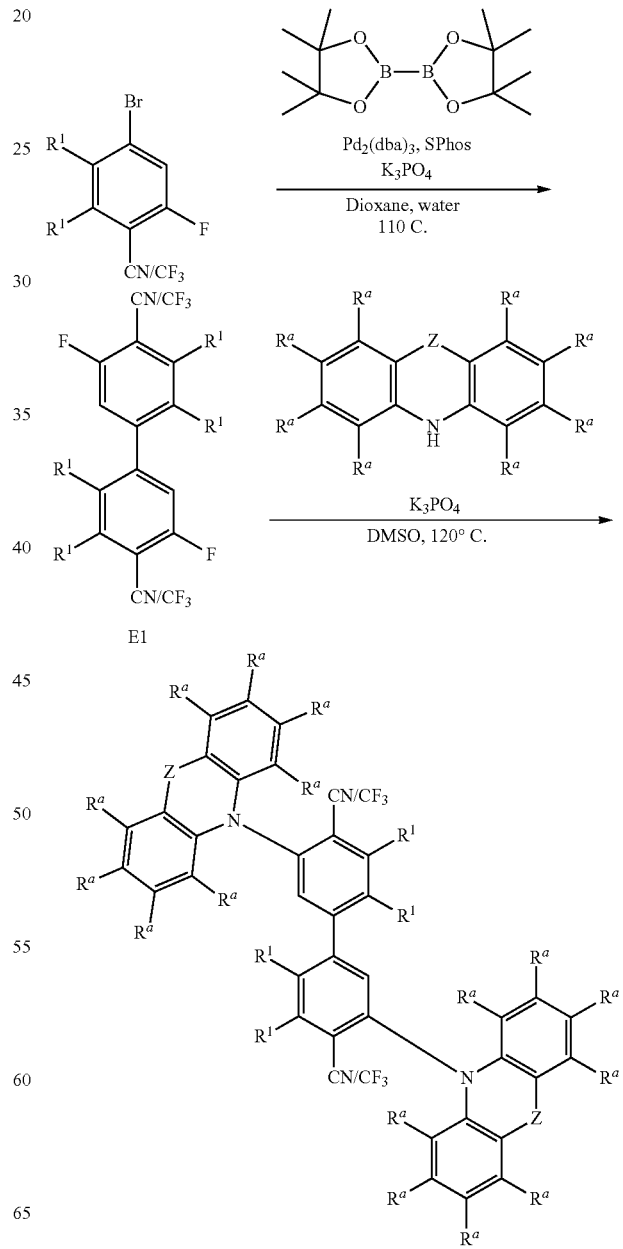

General Synthesis Specification AAV1:

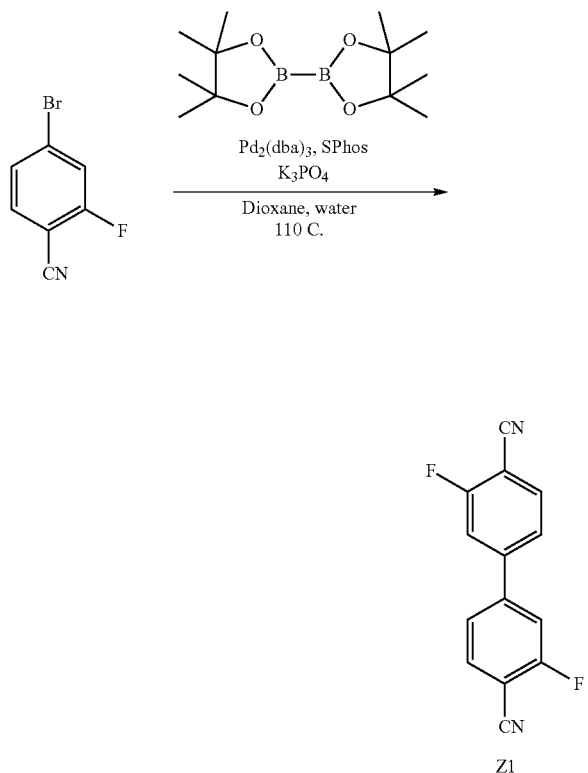

4-bromo-2-fluorobenzonitrile (2.00 equivalent), bis(pinacolato)diboron (1.00 equivalent), pd$_2$(dba)$_3$ (0.01 equivalent), SPhos (0.04 equivalent) and potassium phosphate tribasic (6.00 equivalent) are stirred into a dioxane/water mixture (ratio 20:1) at 110° C. for 16 hours under nitrogen. The insoluble constituents of the reaction mixture are subsequently filtered off and washed with dioxane. The solvent of the filtrate is removed and the obtained residue is dissolved in tetrahydrofuran and filtered through a small amount of silica gel. The product is obtained as a solid.

General Synthesis Specification AAV2:

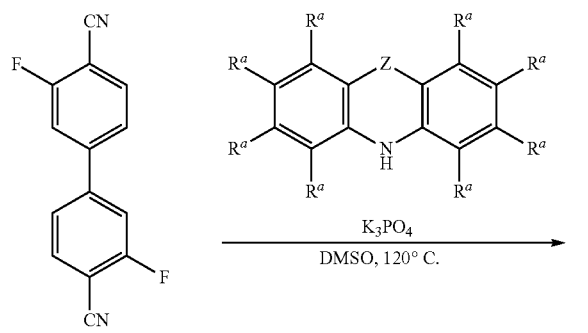

Z1 (1.00 equivalent), the corresponding donor molecule D-H (2.00 equivalent) and potassium phosphate tribasic (4.00 equivalent) are suspended in DMSO under nitrogen and stirred at 110° C. (16 h). The reaction mixture is then added to saturated sodium chloride solution and extracted three times with dichloromethane. The combined organic phases are washed twice with saturated sodium chloride solution, dried over magnesium sulfate, and the solvent is subsequently removed. Lastly, the raw product was purified by recrystallization from toluene. The product is obtained as a solid.

General Synthesis Specification AAV3:

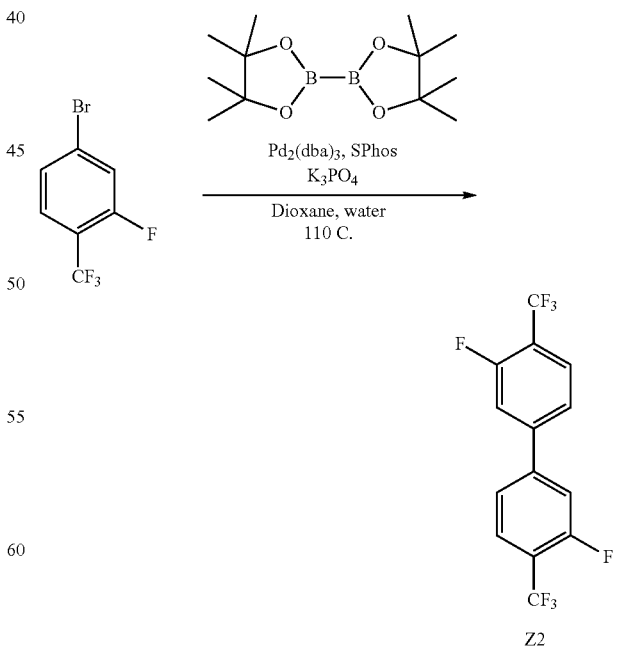

4-bromo-2-fluorobenzotrifluoride (1.00 equivalent), bis(pinacolato)diboron (2.00 equivalent), pd$_2$(dba)$_3$ (0.01 equivalent). SPhos (0.04 equivalent) and potassium phosphate tribasic (6.00 equivalent) are stirred into a dioxane/water mixture (ratio 20:1) at 110° C. for 16 hours under nitrogen. The insoluble constituents of the reaction mixture are subsequently filtered off and washed with dioxane. The solvent of the filtrate is removed and the obtained residue is recrystallized in toluene.

General Synthesis Specification AAV4:

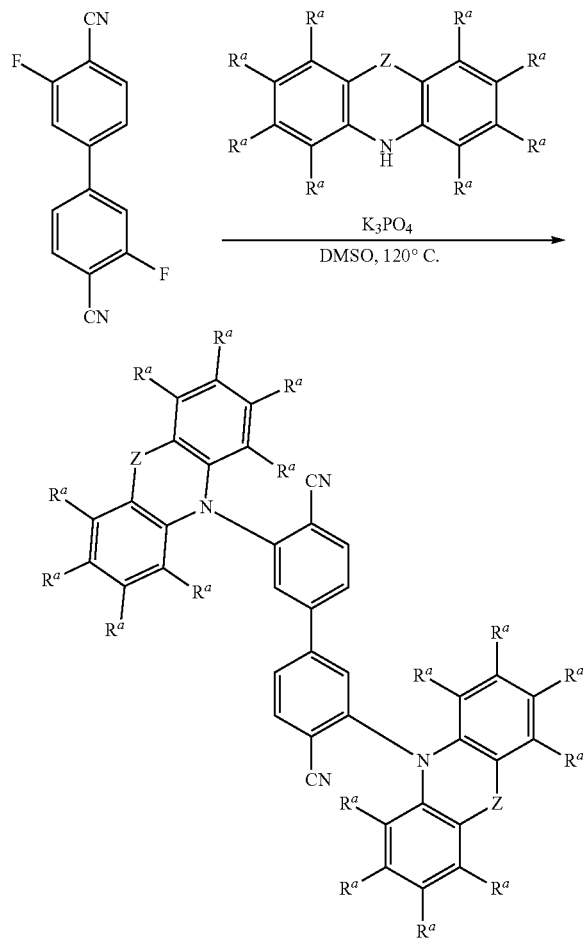

Z2 (1.00 equivalent), the corresponding donor molecule D-H (2.00 equivalent) and potassium phosphate tribasic (4.00 equivalent) are suspended in DMSO under nitrogen and stirred at 110° C. (16 h). The reaction mixture is then added to saturated sodium chloride solution and extracted three times with dichloromethane. The combined organic phases are washed twice with saturated sodium chloride solution, dried over magnesium sulfate, and the solvent is subsequently removed. Lastly, the raw product was purified by recrystallization from toluene. The product is obtained as a solid.

D-H in particular corresponds to a 3,6-substituted carbazole (e.g. 3,6-dimethylcarbazole, 3,6-diphenylcarbazole, 3,6-di-tert-butylcarbazole), a 2,7-substituted carbazole (e.g. 2,7-dimethylcarbazole, 2,7-diphenylcarbazole, 2,7-di-tert-butylcarbazole), an 1,8-substituted carbazole (e.g. 1,8-dimethylcarbazole, 1,8-diphenylcarbazole, 1,8-di-tert-butylcarbazole), a 1-substituted carbazole (e.g. 1-methylcarbazole, 1-phenylcarbazole, 1-tert-butylcarbazole), a 2-substituted carbazole (e.g. 2-methylcarbazole, 2-phenylcarbazole, 2-tert-butylcarbazole) or a 3-substituted carbazole (e.g. 3-methylcarbazole, 3-phenylcarbazole, 3-tert-butylcarbazole).

Photophysical Measurements

Pretreatment of Optical Glasses

All glasses (cuvettes and substrates made of quartz glass, diameter: 1 cm) were cleaned after every use: In each case washed three times with dichloromethane, acetone, ethanol, demineralized water, placed in 5% Hellmanex solution for 24 h, thoroughly rinsed with demineralized water. The optical glasses were dried by blowing nitrogen over them.

Sample Preparation, Film: Spin Coating

Device: Spin150, SPS Euro.

The sample concentration was equivalent to 10 mg/ml, prepared in toluene or chlorobenzene.

Program: 1) 3 s at 400 rpm; 2) 20 s at 1000 rpm at 1000 rpm/s. 3) 10 s at 4000 rpm at 1000 rpm/s. After coating, the films were dried on a LHG precision heating plate for 1 min at 70° C. in air.

Photoluminescence Spectroscopy and TCSPC

Steady-state emission spectroscopy was carried out using a fluorescence spectrometer of the Horiba Scientific company, Model Fluoromax-4, equipped with a 150 W xenon arc lamp, excitation and emission monochromators and a Hamamatsu R928 photomultiplier tube, as well as a "Time-Correlated Single Photon Counting" (TCSPC) option. The emission and excitation spectra were corrected by means of standard correction curves.

The emission decay times were likewise measured on this system, using the TCSPC method with the FM-2013 accessories and a TCSPC hub of the Horiba Yvon Jobin company.

Excitation Sources:

NanoLED 370 (wavelength: 371 nm, pulse duration: 1.1 ns)

NanoLED 290 (wavelength: 294 nm, pulse duration: <1 ns)

SpectraLED 310 (wavelength: 314 nm)

SpectraLED 355 (wavelength: 355 nm).

The analysis (exponential fitting) was performed using the DataStation software package and the DAS6 analysis software. The fit was specified with the aid of the Chi-square method $$c^2 = \sum_{k=1}^{i} \frac{(e_i - o_i)^2}{e_i}$$

with $e_i$: variable predicted by the fit and $o_i$: measured variable.

Quantum Efficiency Determination

The measurement of the photoluminescence quantum yield (PLQY) was carried out by means of an Absolute PL Quantum Yield Measurement C9920-03G system of the Hamamatsu Photonics company. Said system consists of a 150 W xenon gas discharge lamp, automatically adjustable Czerny-Turner monochromators (250-950 nm) and an Ulbricht sphere with a high reflectance Spectralon coating (a Teflon derivative), which is connected via a fiber optic cable to a PMA-12 multichannel detector with a BT (back-thinned)-CCD chip having 1024×122 pixels (size 24×24 µm). The analysis of the quantum efficiency and the CIE coordinates was carried out using the software U6039-05 Version 3.6.0.

The emission maximum is measured in nm, the quantum yield Φ is measured in % and the CIE color coordinates are stated as x, y values.

The photoluminescence quantum yield was determined according to the following protocol:

1) Implementation of quality assurance measures: Anthracene in ethanol at a known concentration serves as the reference material.

2) Determination of the excitation wavelength: The absorption maximum of the organic molecule was first determined and excited with said wavelength.

3) Implementation of the sample measurement:

The absolute quantum yield of degassed solutions and films was determined under a nitrogen atmosphere.

The calculation was performed within the system according to the following equation:

$$\Phi_{PL} = \frac{n_{photon}, \text{emitted}}{n_{photon}, \text{absorbed}} = \frac{\int \frac{\lambda}{hc}\left[Int_{emitted}^{sample}(\lambda) - Int_{absorbed}^{sample}(\lambda)\right]d\lambda}{\int \frac{\lambda}{hc}\left[Int_{emitted}^{reference}(\lambda) - Int_{absorbed}^{reference}(\lambda)\right]d\lambda}$$

with the photon number $n_{photon}$ and the intensity Int.

Production and characterization of organic electroluminescence devices from the gas phase With the organic molecules according to the invention, OLED devices can be produced by means of vacuum sublimation techniques.

These not yet optimized OLEDs can be characterized in the usual manner. To do this, the electroluminescence spectra, the external quantum efficiency (measured in %) as a function of the brightness and calculated from the light detected by the photodiode, the electroluminescence spectra and the current are recorded.

Example 1

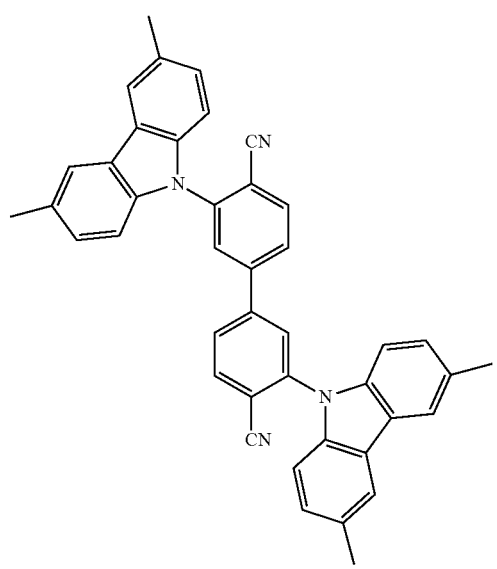

Example 1 was produced in accordance with AAV1 (Yield 45%) and AAV2 (Yield 64%).

FIG. 1 shows the emission spectrum of Example 1 (10% in PMMA). The emission maximum is at 489 nm. The photoluminescence quantum yield (PLQY) is 63% and the full width at half maximum is 0.46 eV.

Example 2

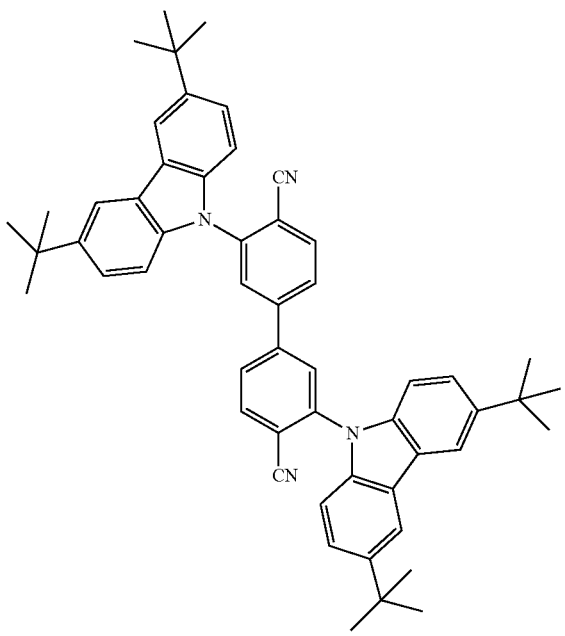 [SMILES: CC(C)(C)c1ccc2c(c1)c1cc(C(C)(C)C)ccc1n2-c1cc(-c2ccc(C#N)c(-n3c4ccc(C(C)(C)C)cc4c4cc(C(C)(C)C)ccc43)c2)ccc1C#N]

Example 2 was produced in accordance with AAV1 (Yield 45%) and AAV2 (Yield 78%).

Figure 2:
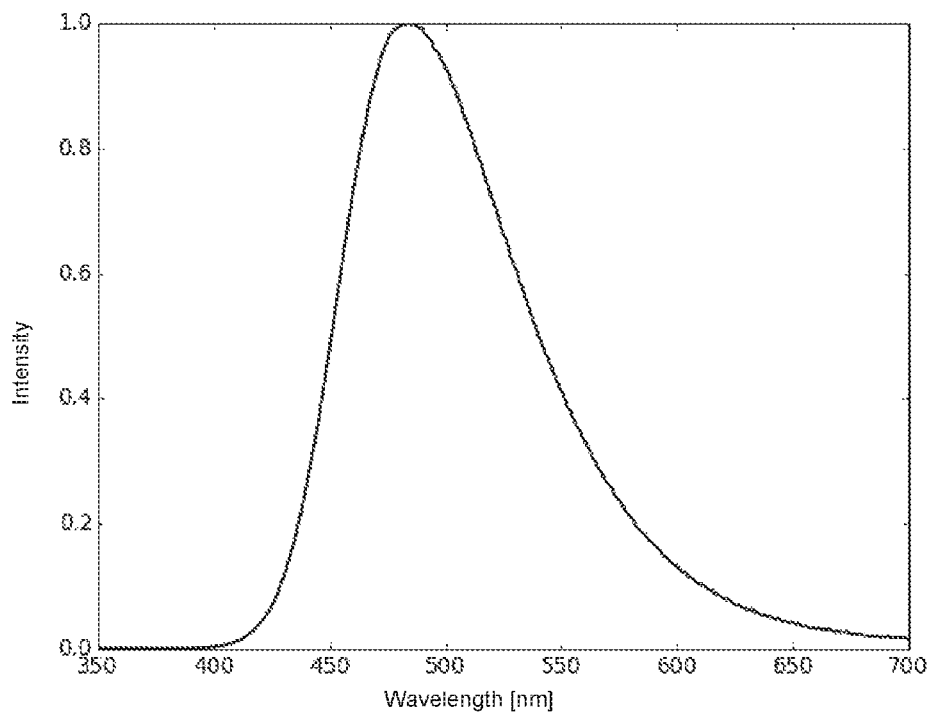
FIG. 2 is an Emission spectrum of Example 2 in 10% PMMA.

FIG. 2 shows the emission spectrum of Example 2 (10% in PMMA). The emission maximum is at 484 nm. The photoluminescence quantum yield (PLQY) is 75% and the full width at half maximum is 0.46 eV.

Example 3

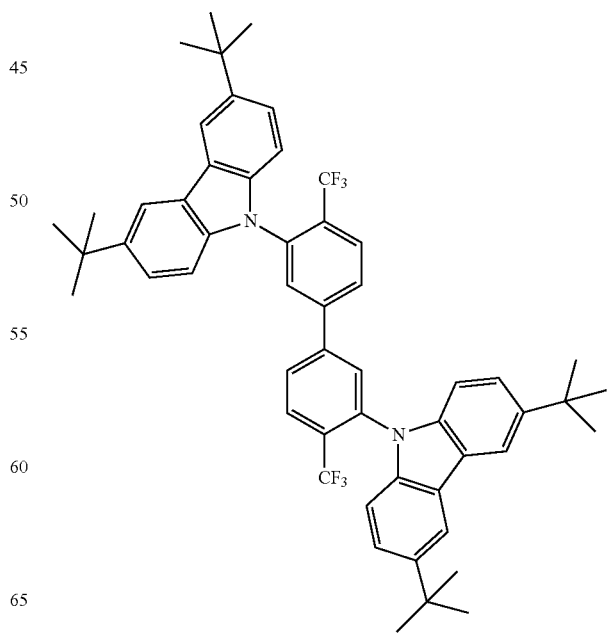

Example 3 was produced in accordance with AAV3 (Yield 32%) and AAV4 (Yield 16%).

Thin layer chromatography: $R_f$=0.74 (cyclohexane/ethylacetate 5:1)

Figure 3:
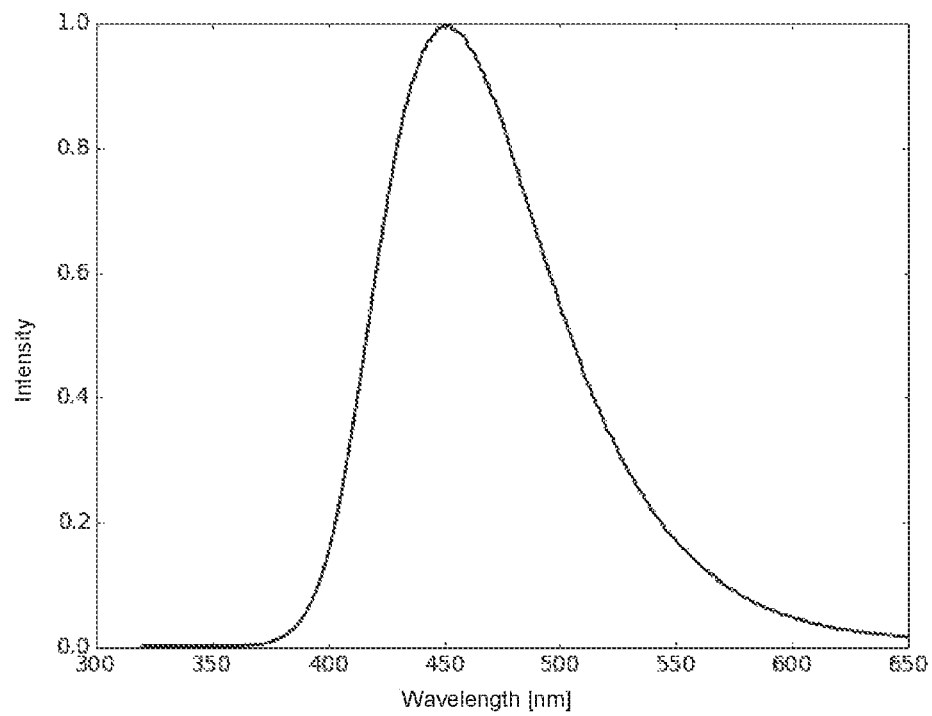
FIG. 3 is an Emission spectrum of Example 3 in 10% PMMA.

FIG. 3 shows the emission spectrum of Example 3 (10% in PMMA). The emission maximum is at 450 nm. The photoluminescence quantum yield (PLQY) is 66% and the full width at half maximum is 0.52 eV.

Example 4

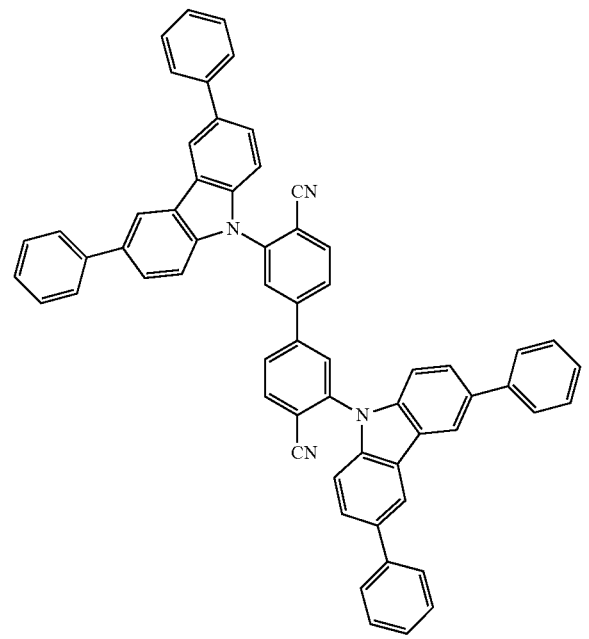 [SMILES: N#Cc1ccc(-c2ccc(C#N)c(-n3c4ccc(-c5ccccc5)cc4c4cc(-c5ccccc5)ccc43)c2)cc1-n1c2ccc(-c3ccccc3)cc2c2cc(-c3ccccc3)ccc21]

Example 4 was produced in accordance with AAV1 (Yield 45%) and AAV2 (Yield 58%).

Figure 4:
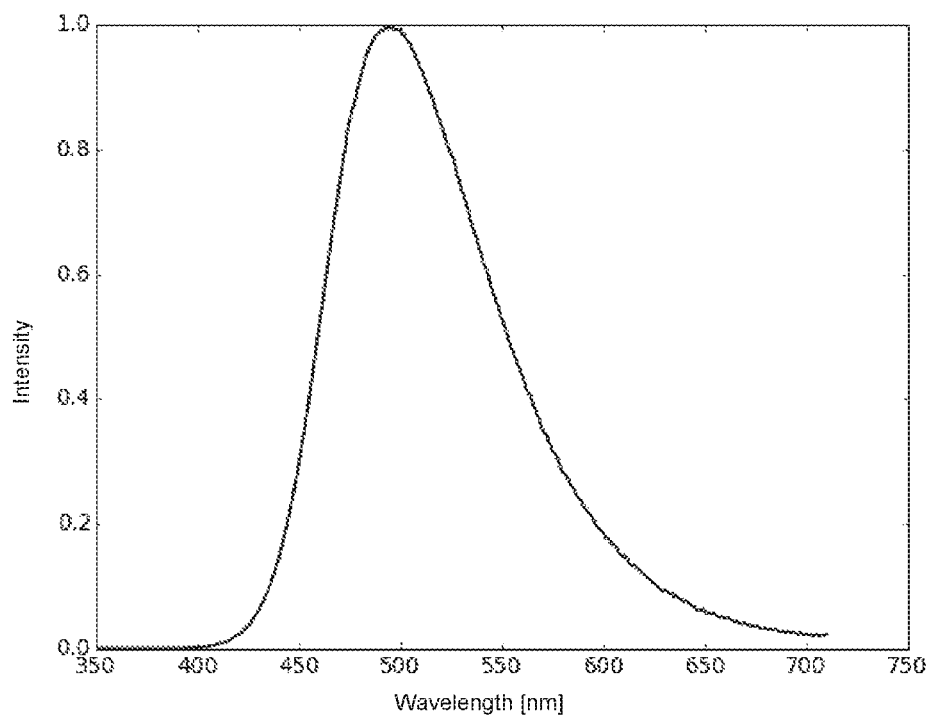
FIG. 4 is an Emission spectrum of Example 4 in 10% PMMA.

FIG. 4 shows the emission spectrum of Example 4 (10% in PMMA). The emission maximum is at 495 nm. The photoluminescence quantum yield (PLQY) is 62% and the full width at half maximum is 0.45 eV.

Example 5

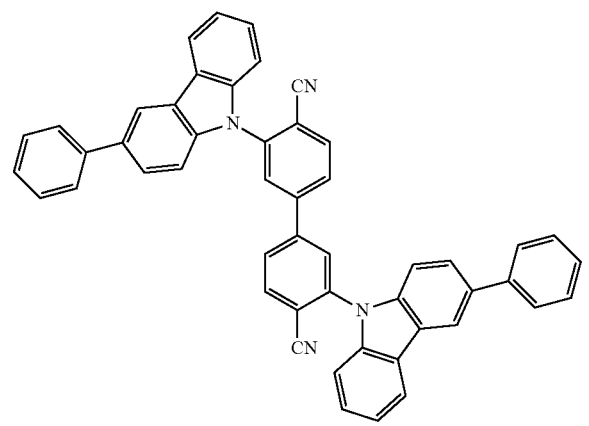 [SMILES: N#Cc1ccc(-c2ccc(C#N)c(-n3c4ccccc4c4cc(-c5ccccc5)ccc43)c2)cc1-n1c2ccccc2c2cc(-c3ccccc3)ccc21]

Example 5 was produced in accordance with AAV1 (Yield 45%) and AAV2 (Yield 73%).

Figure 5:
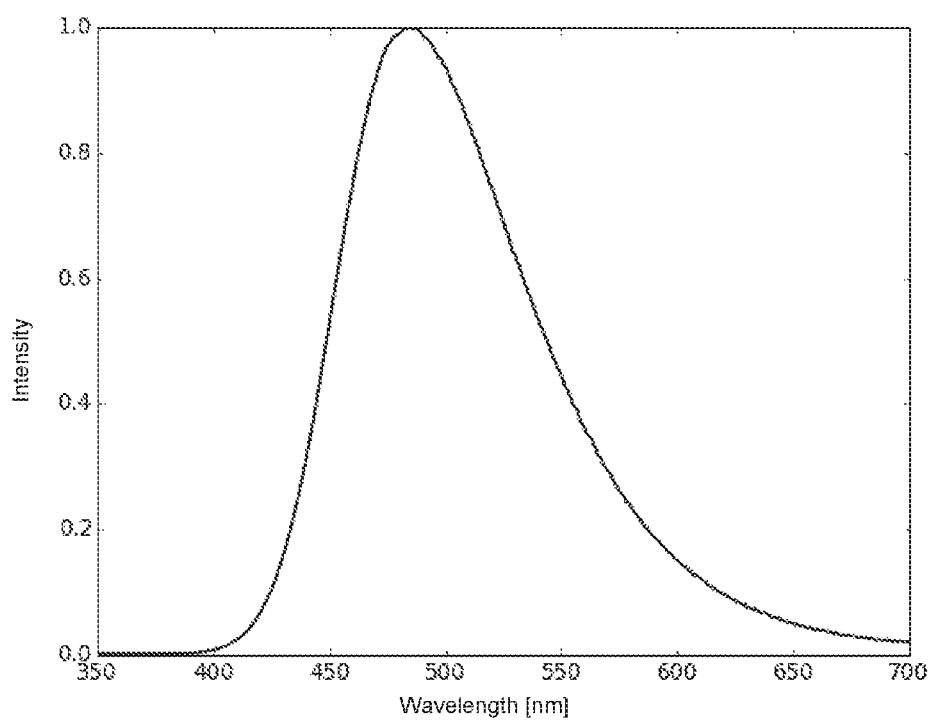
FIG. 5 is an Emission spectrum of Example 5 in 10% PMMA.

FIG. 5 shows the emission spectrum of Example 5 (10% in PMMA). The emission maximum is at 484 nm. The photoluminescence quantum yield (PLQY) is 54% and the full width at half maximum is 0.49 eV.

Example 6

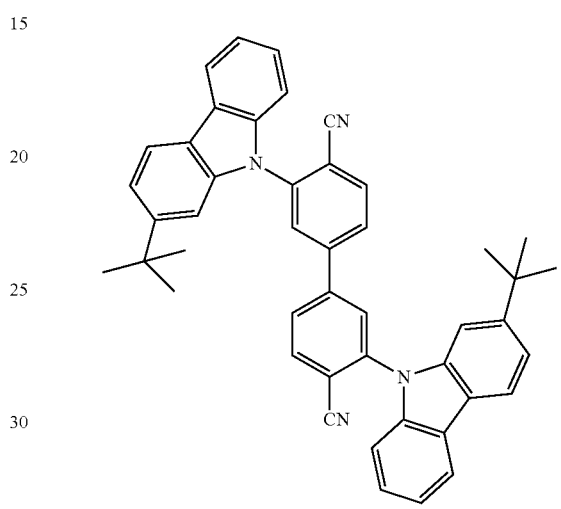

Example 6 was produced in accordance with AAV1 (Yield 45%) and AAV2 (Yield 73%).

The emission maximum is at 472 nm. The photoluminescence quantum yield (PLQY) is 67% and the full width at half maximum is 0.46 eV.

Further examples of organic molecules having a structure according to Formula I:

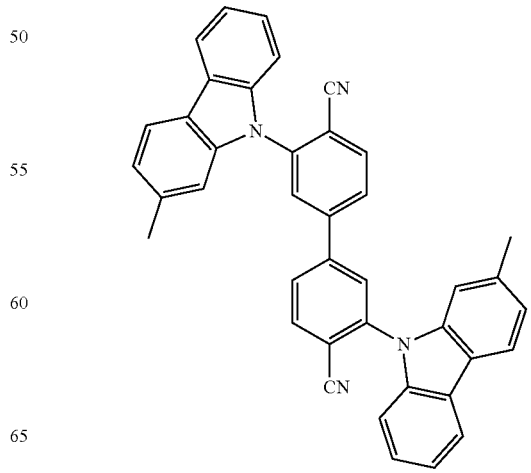

25
-continued
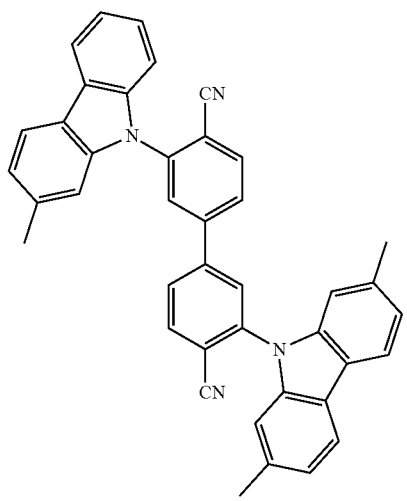
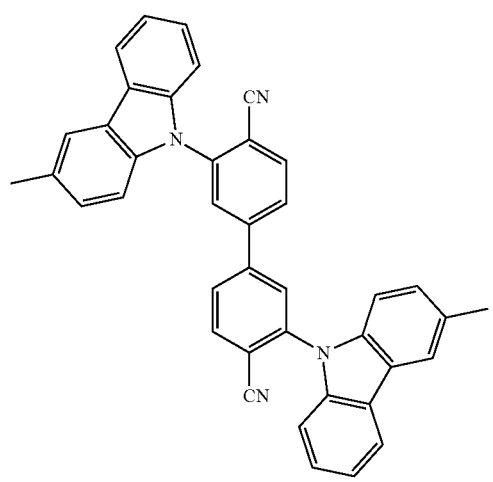
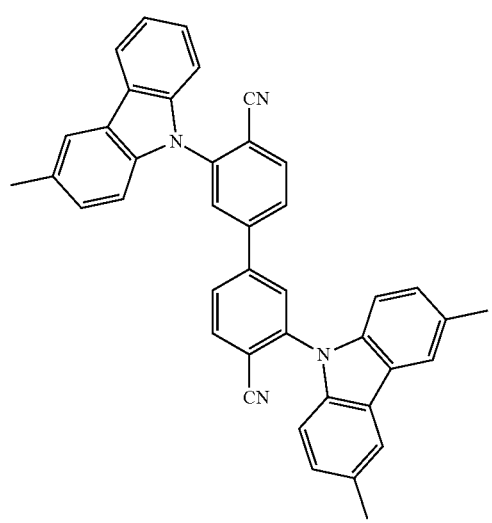
26
-continued
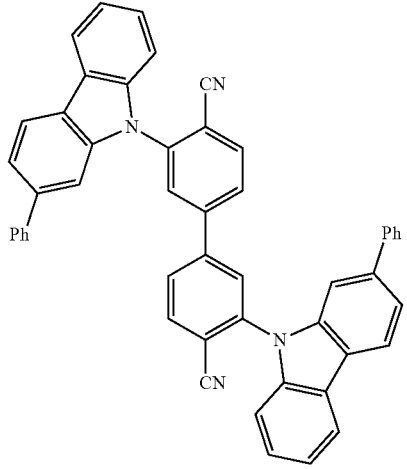
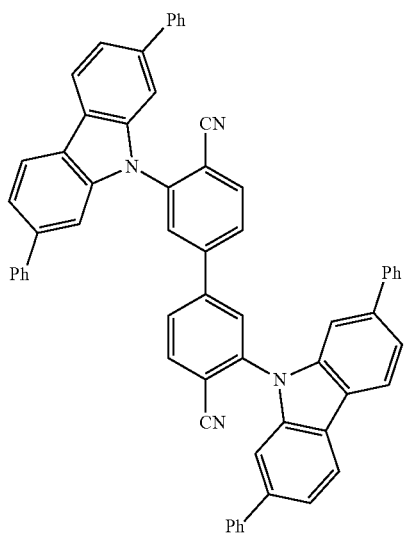
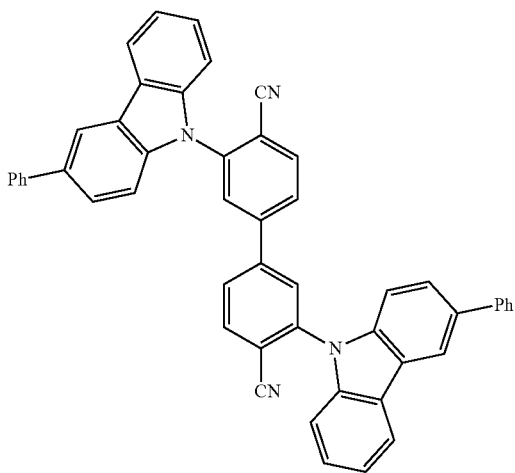

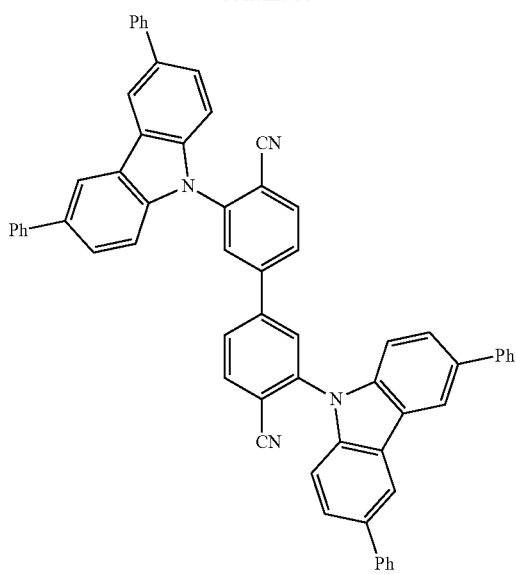
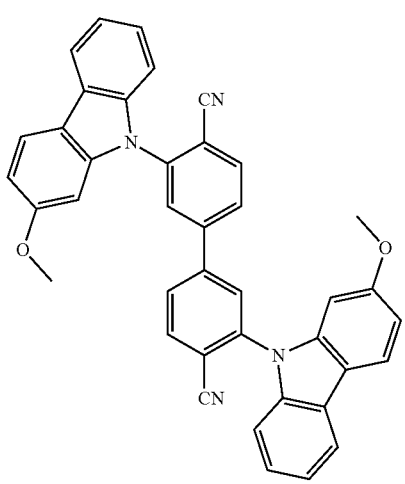
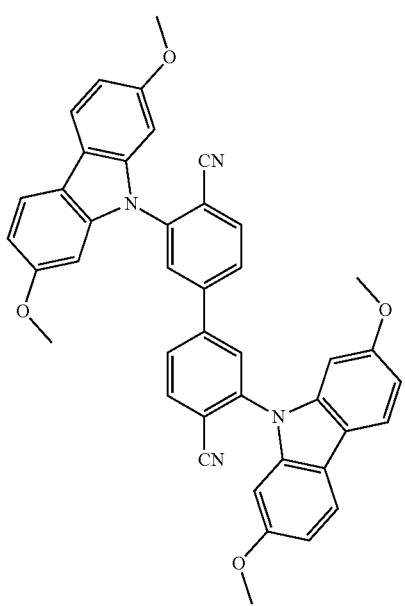
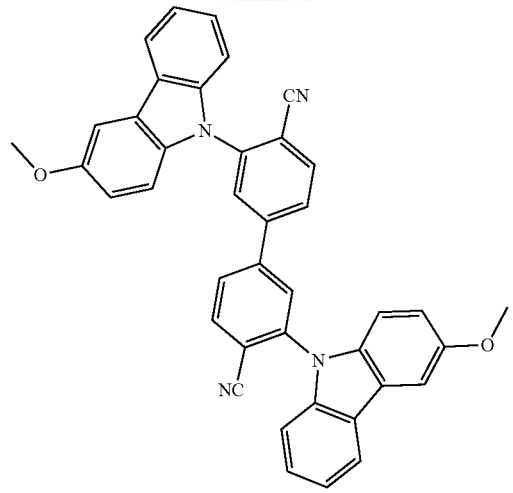
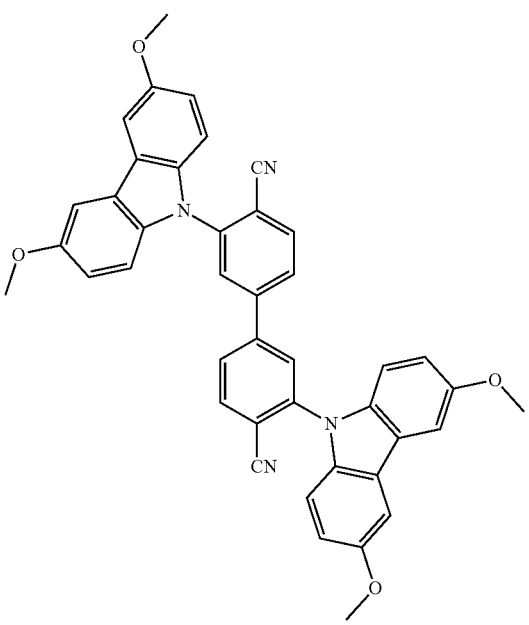
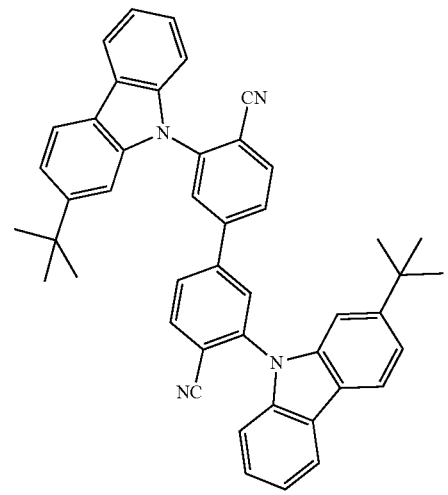

29
-continued
30
-continued
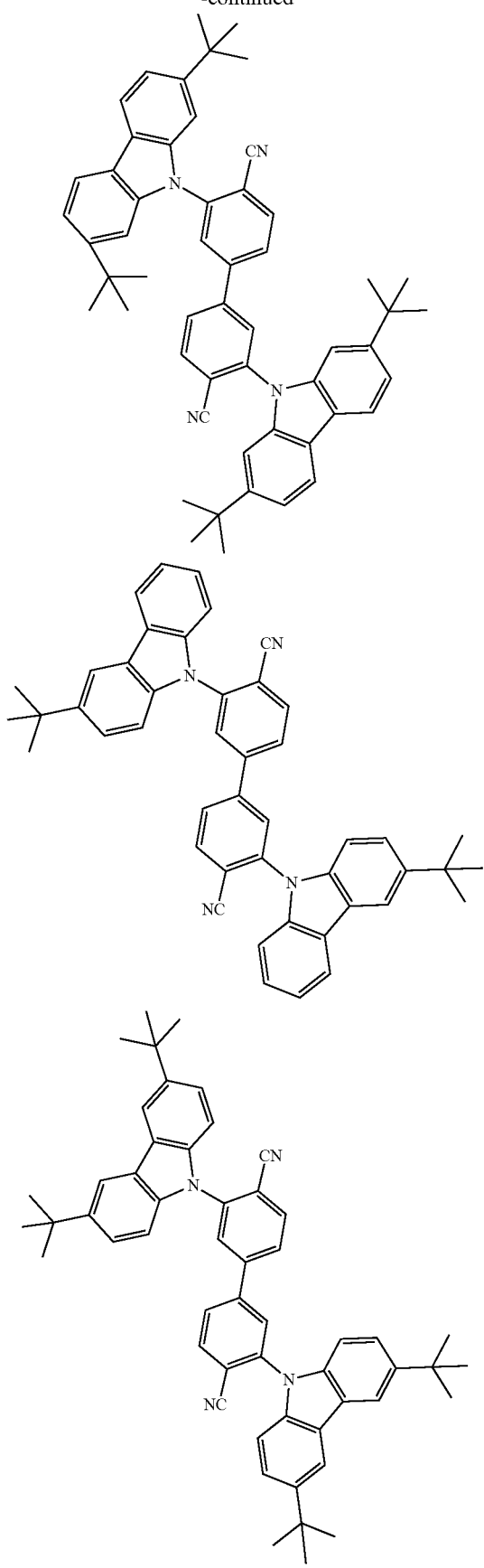
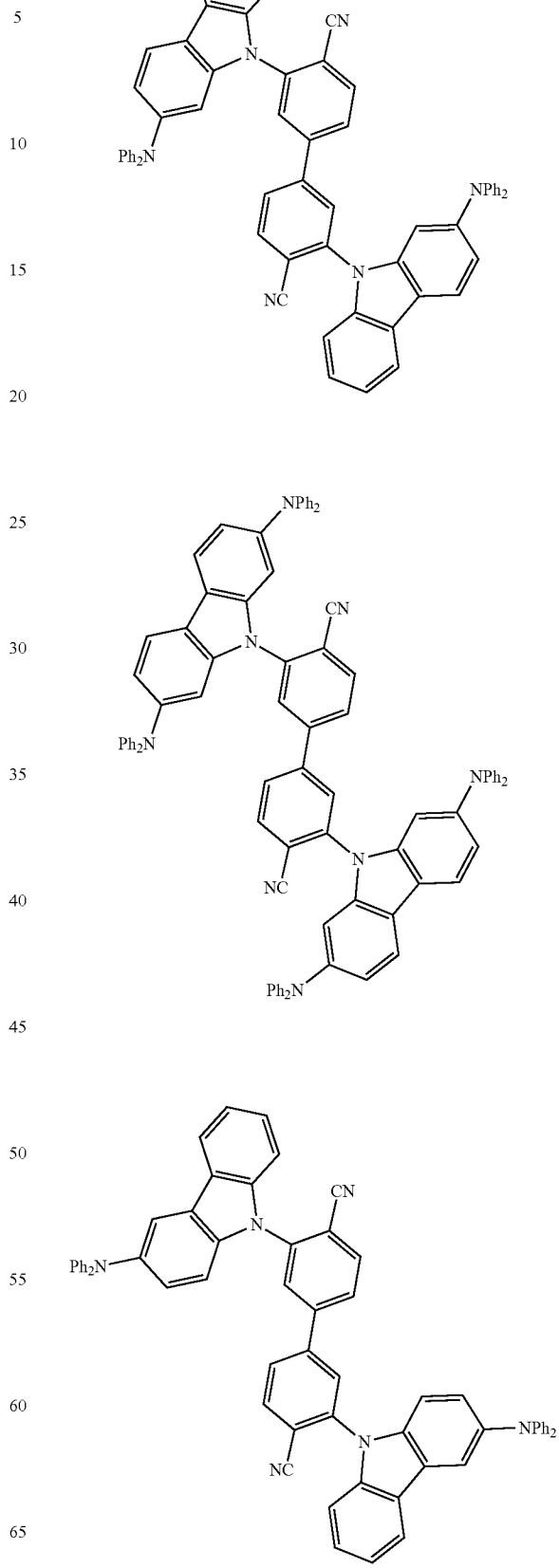

31
-continued
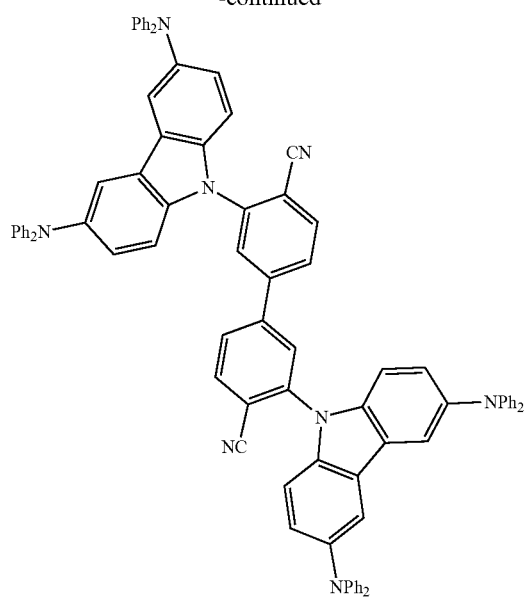
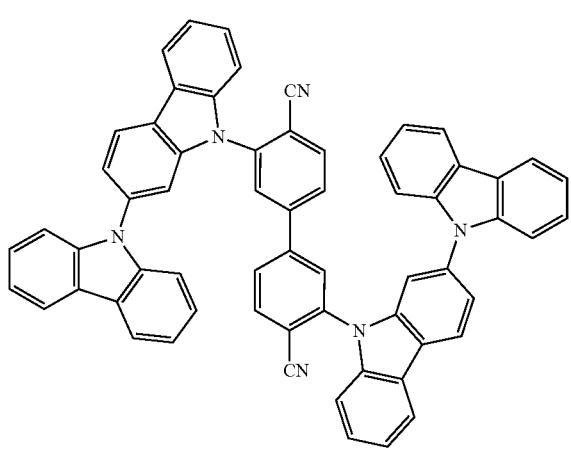
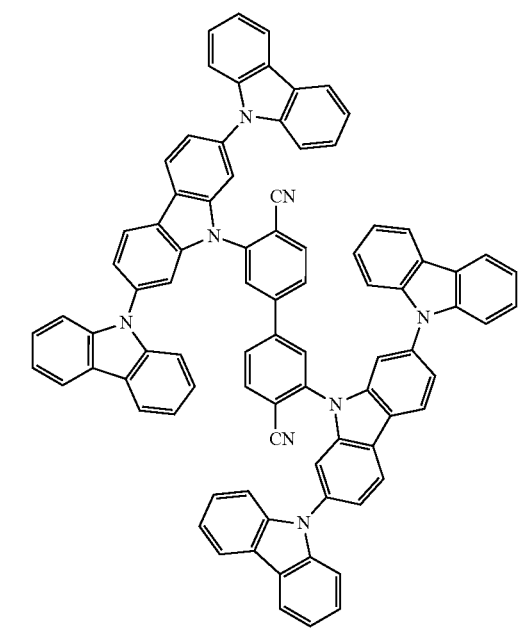
32
-continued
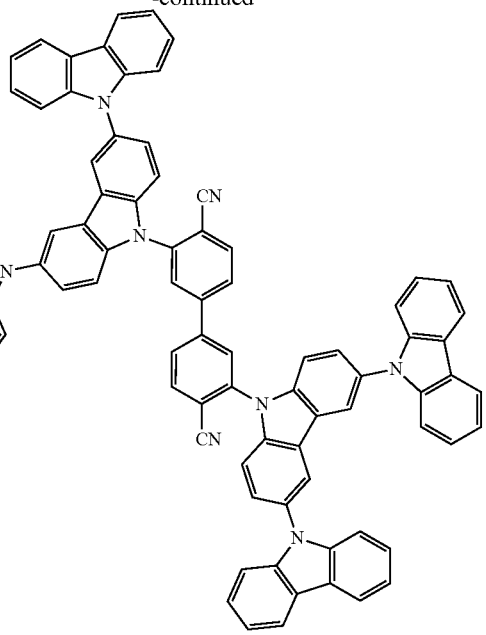
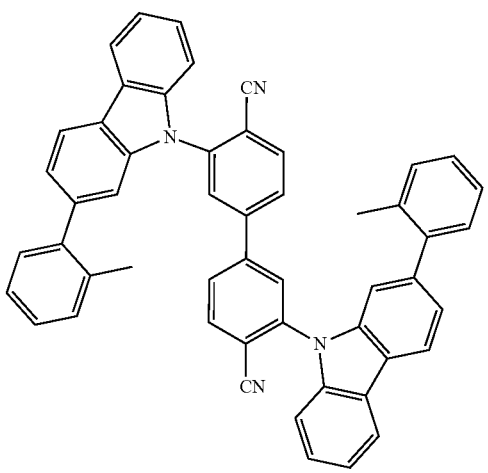

33
-continued
34
-continued
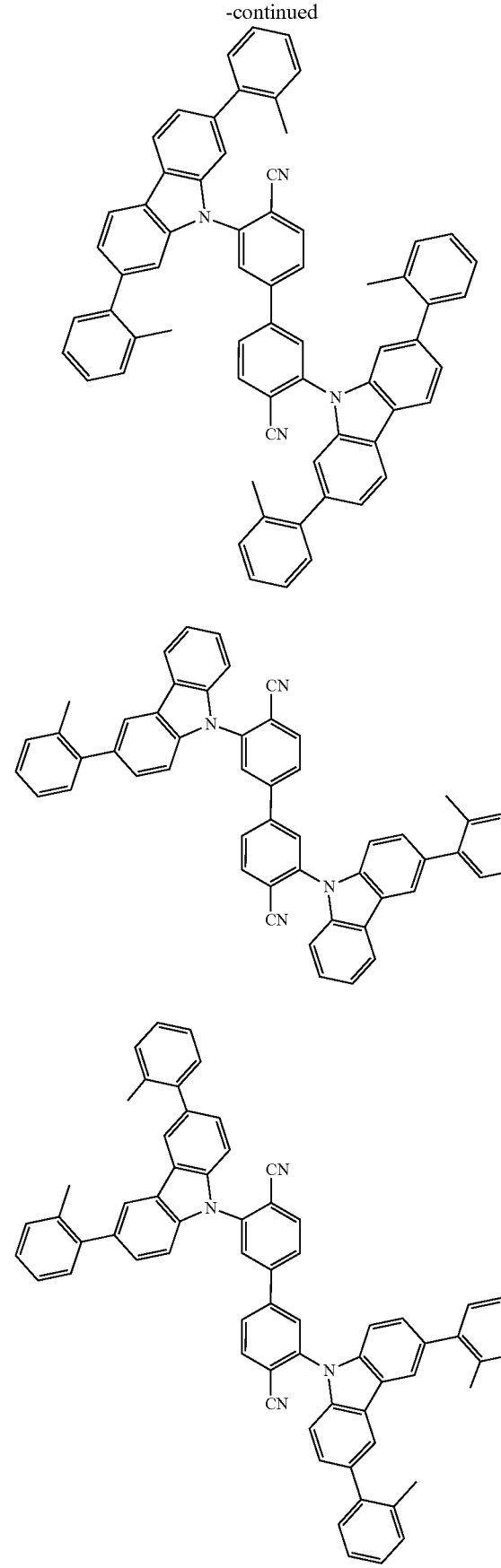
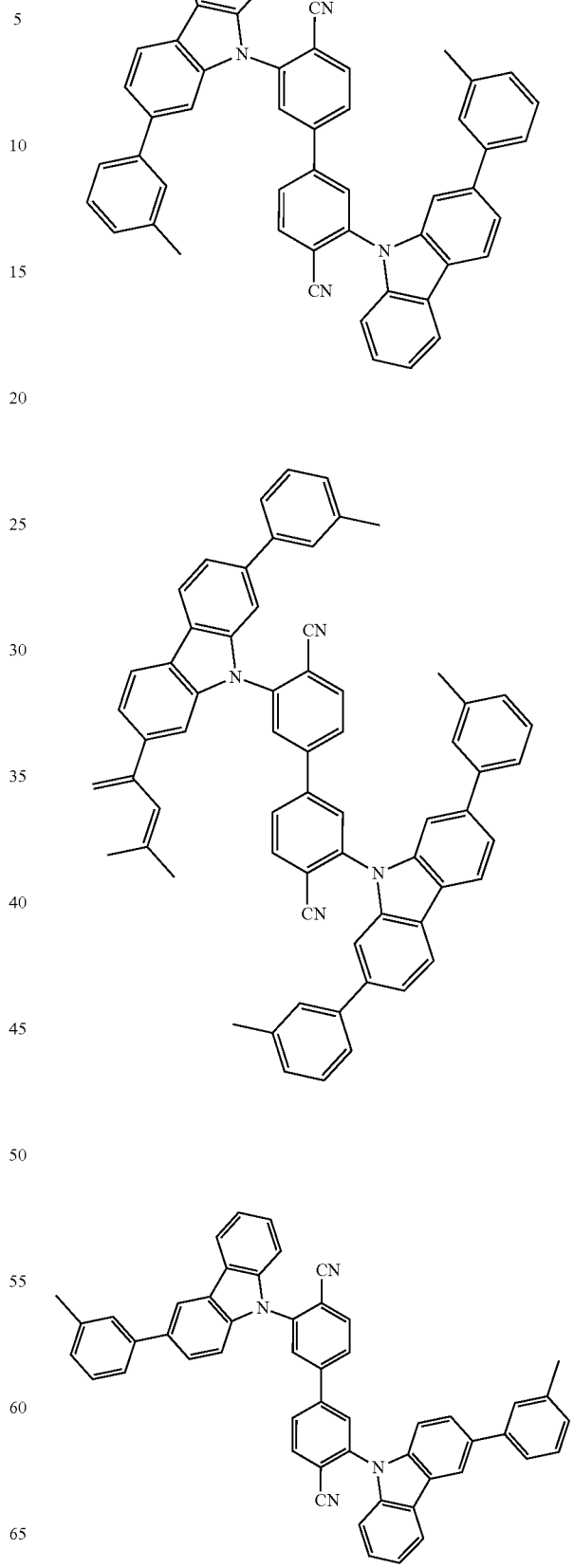

35
-continued
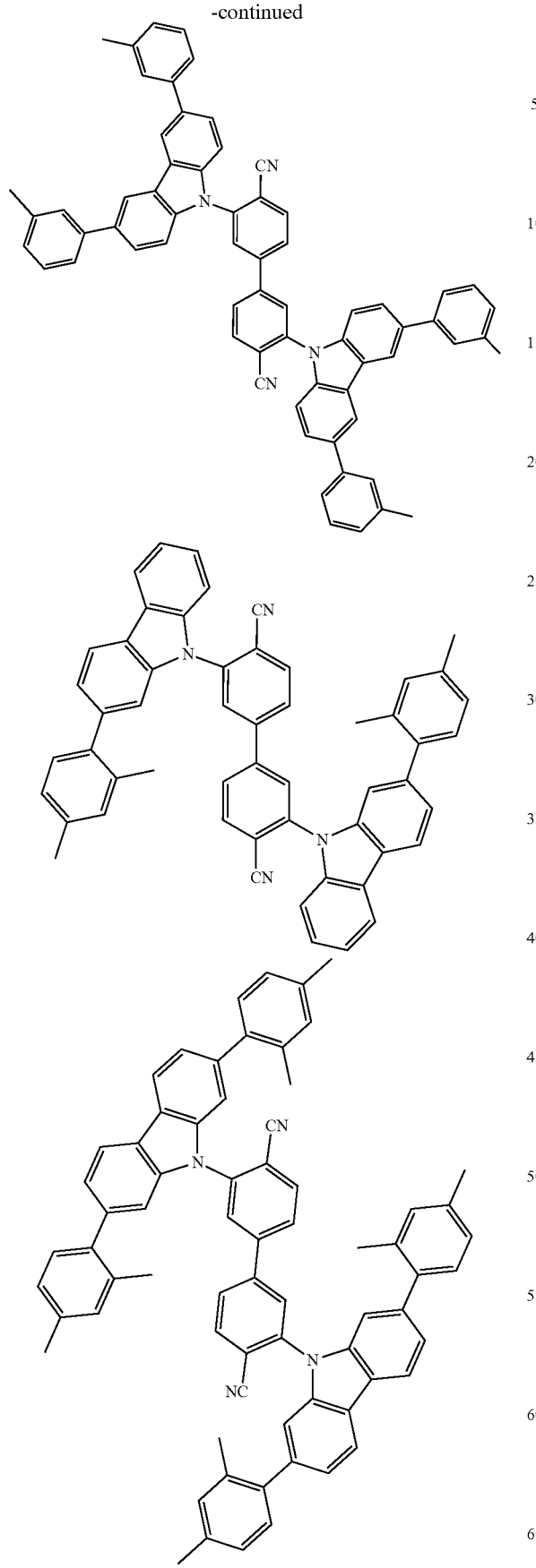
36
-continued
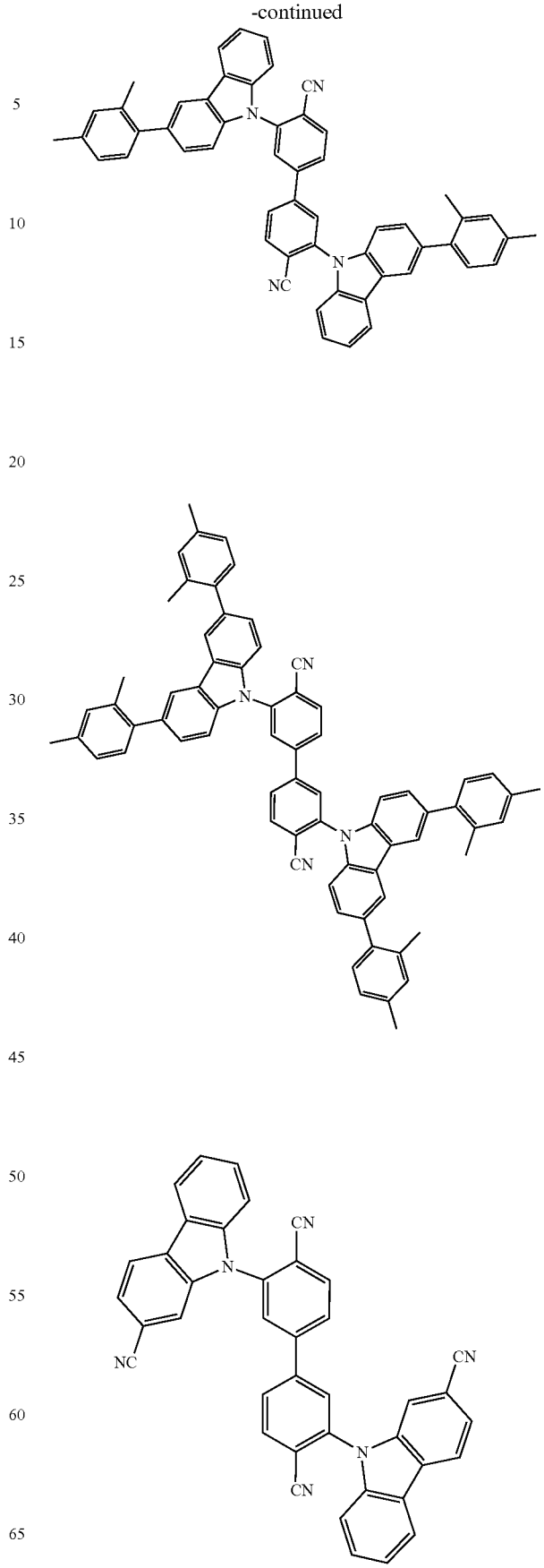

-continued
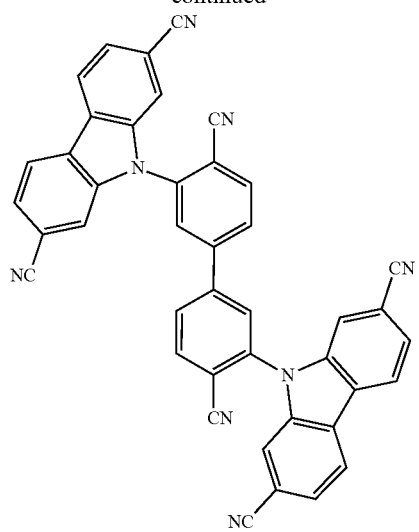
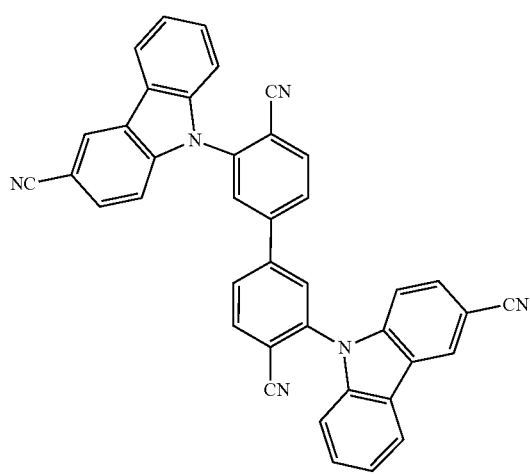
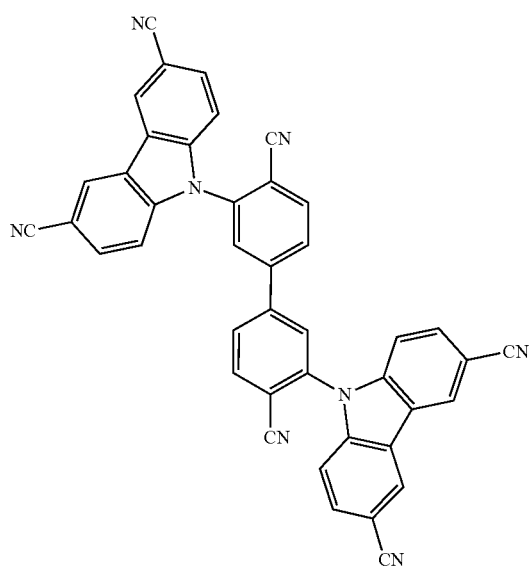
-continued
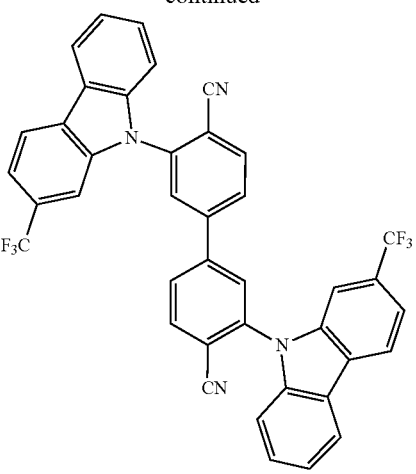
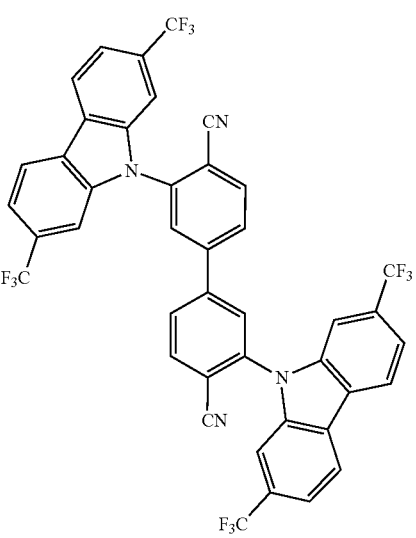
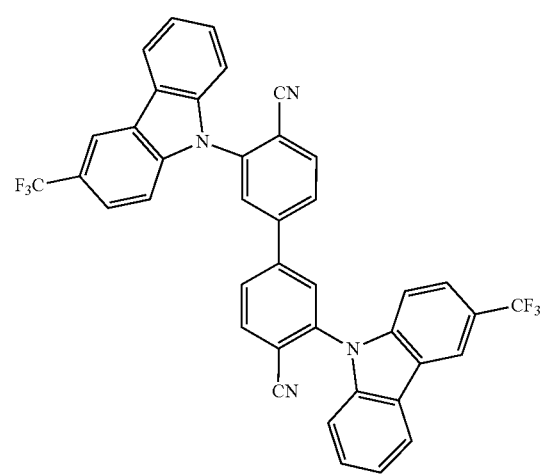

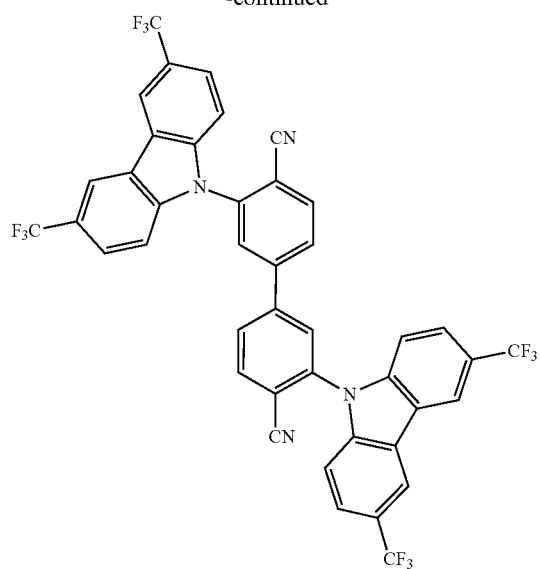
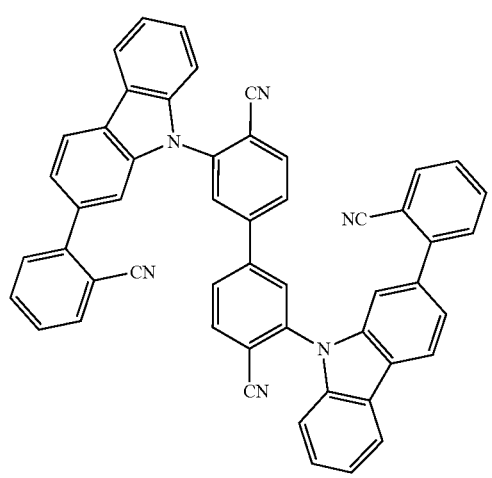
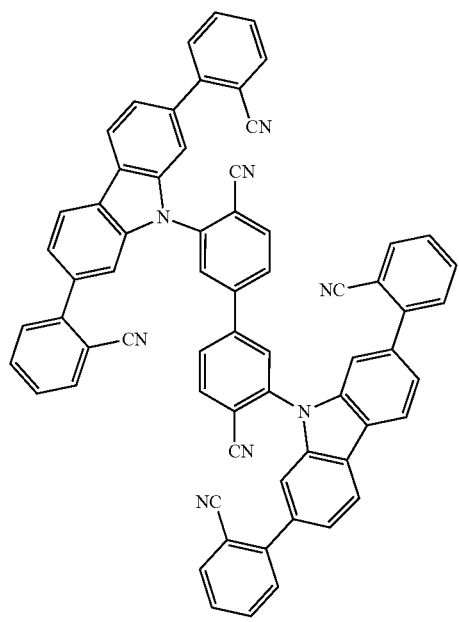
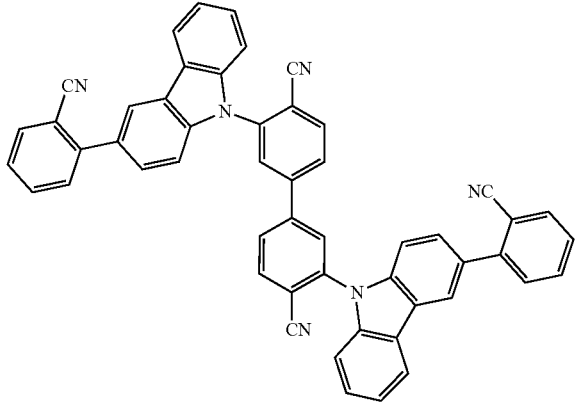
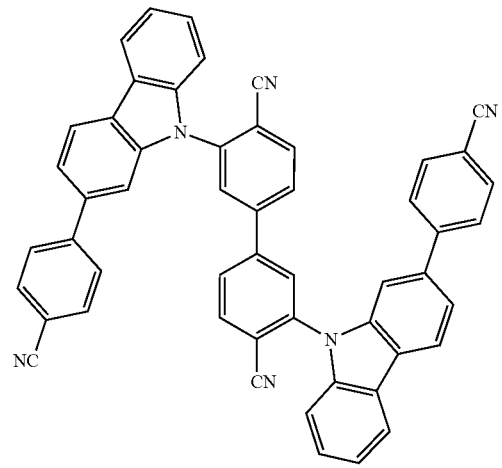

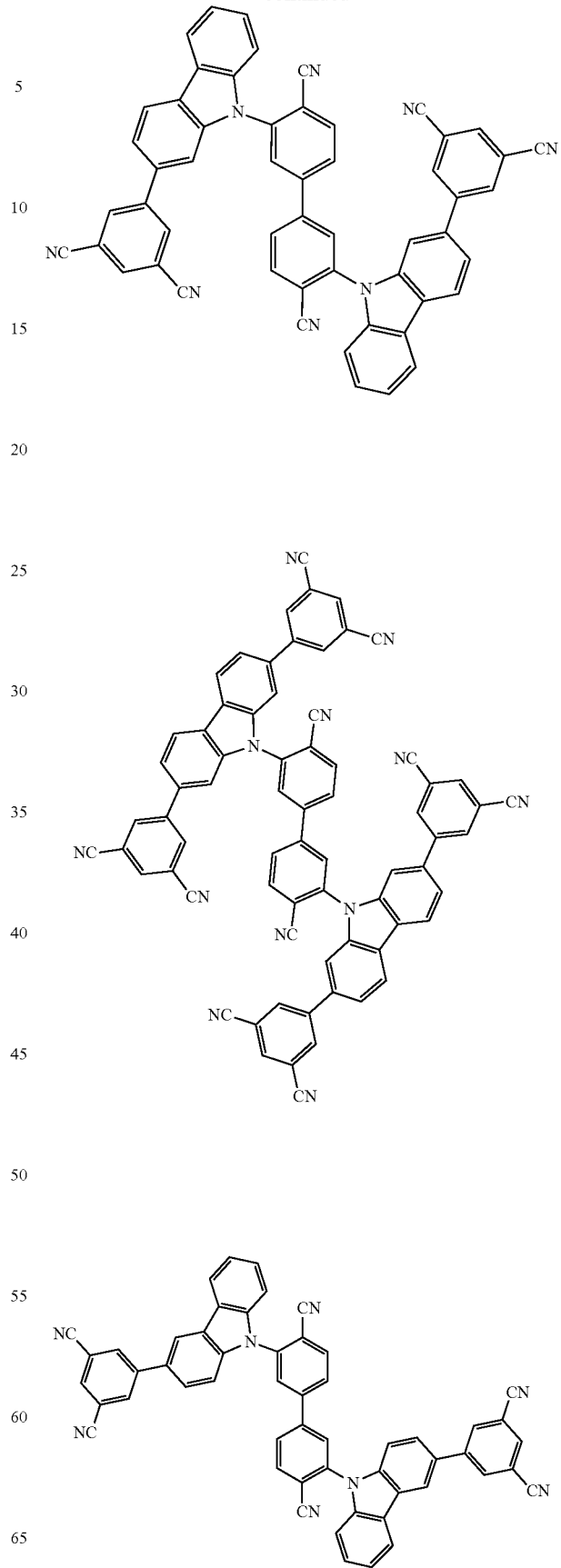

43
-continued
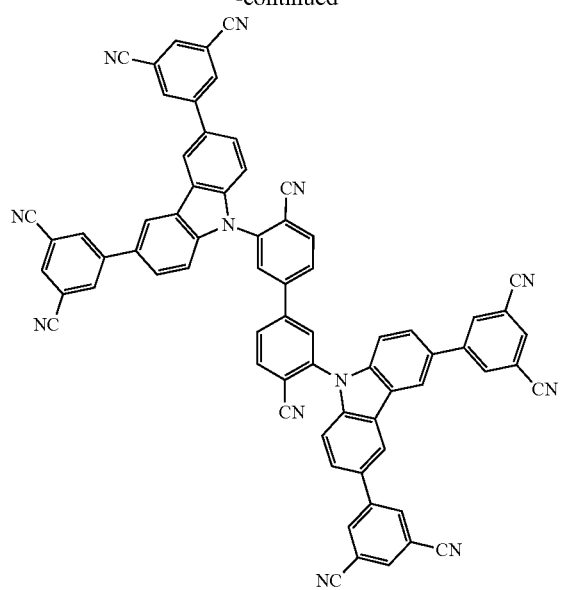
44
-continued
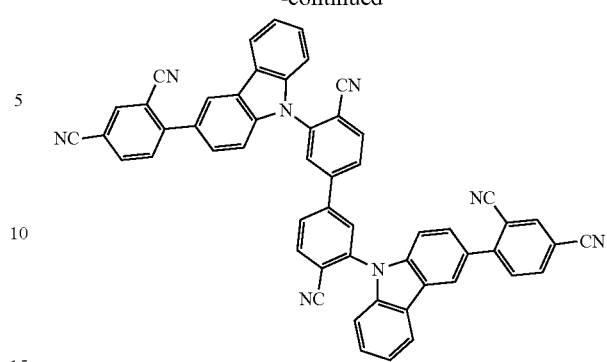
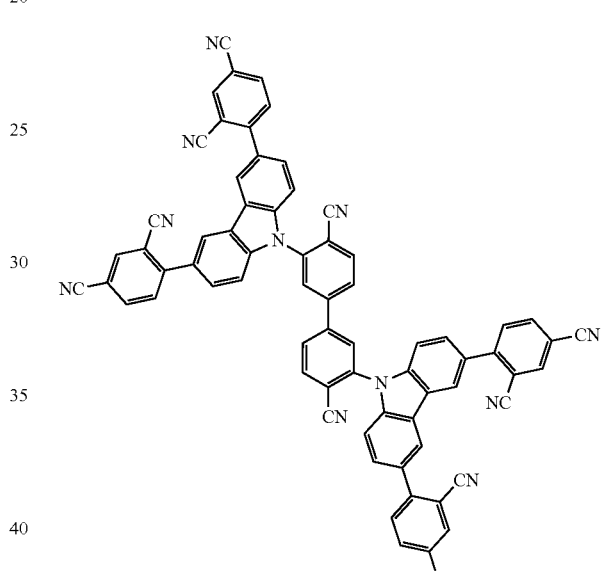
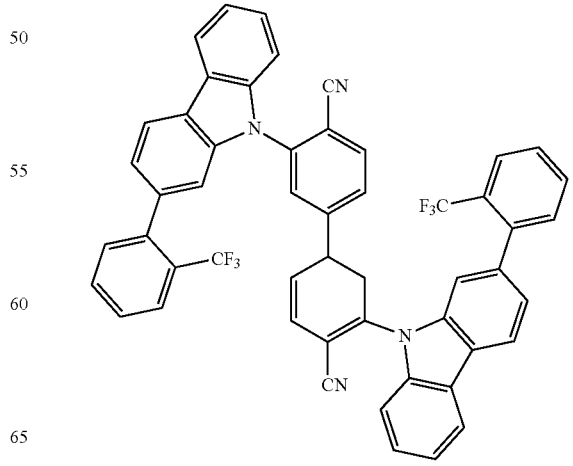

45
-continued
46
-continued
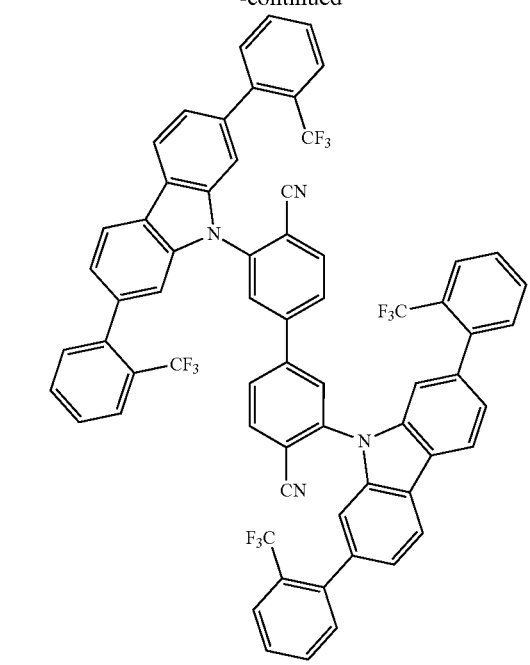
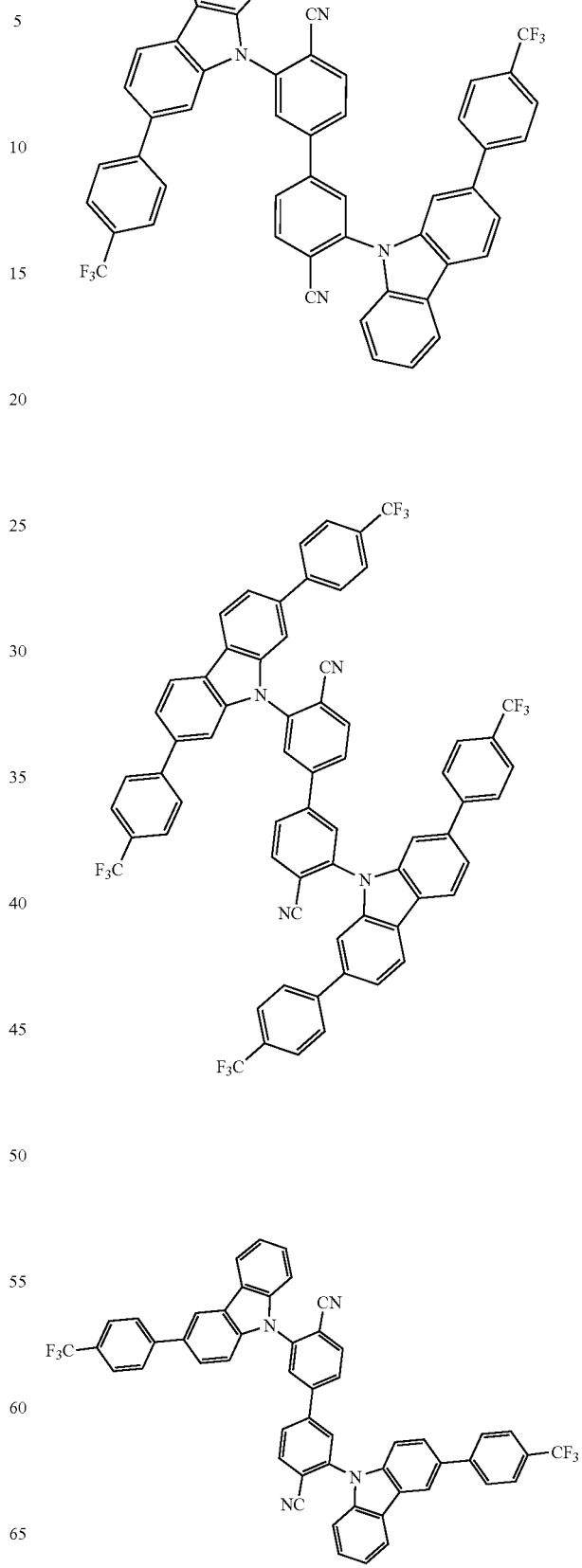

47
-continued
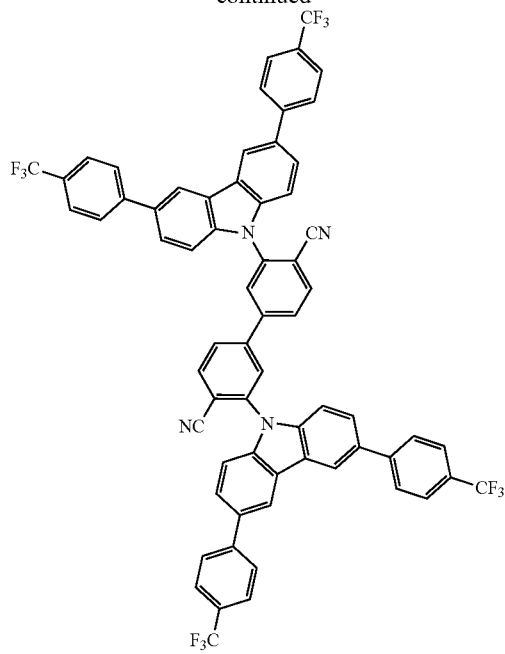
48
-continued
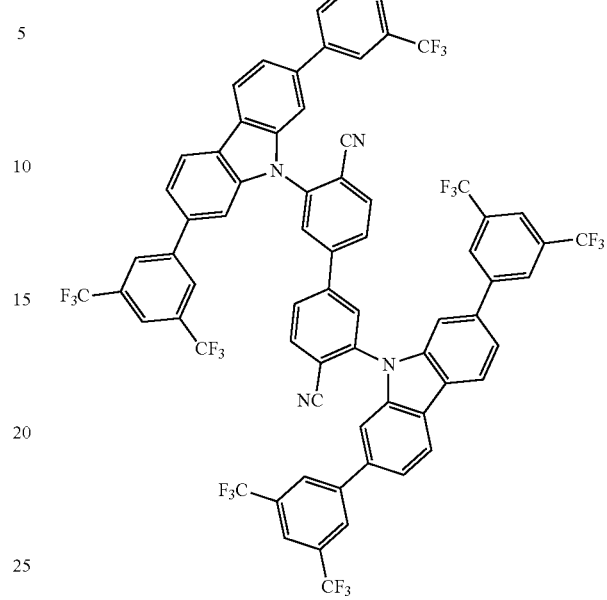
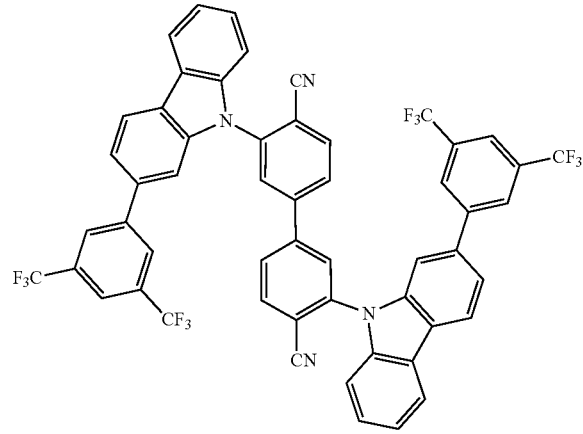
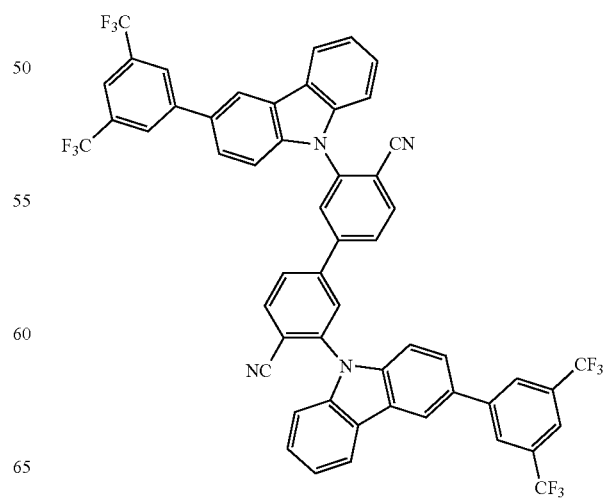

-continued
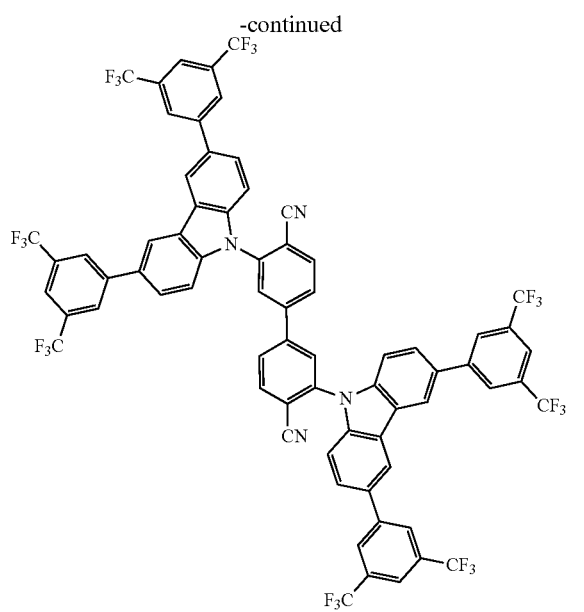
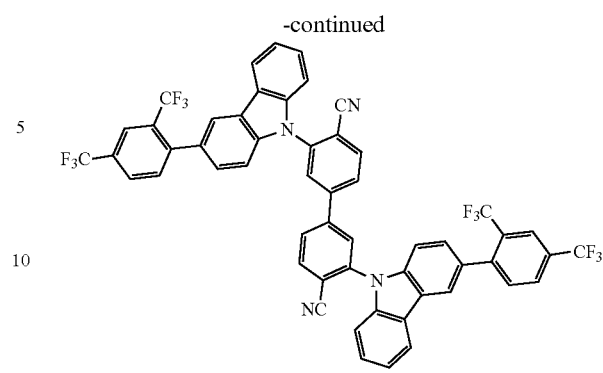
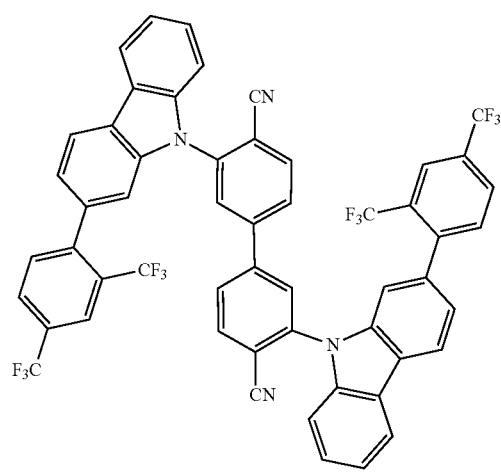
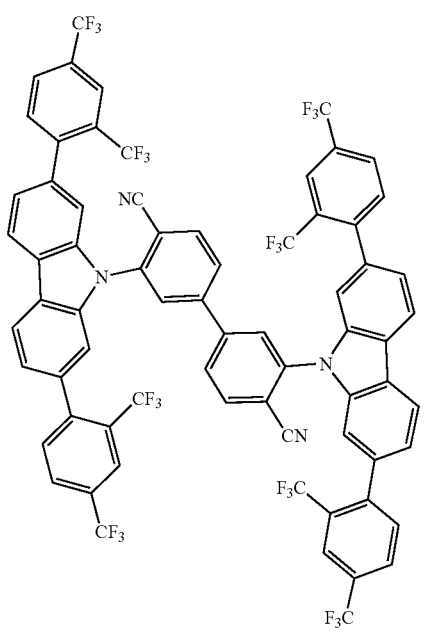
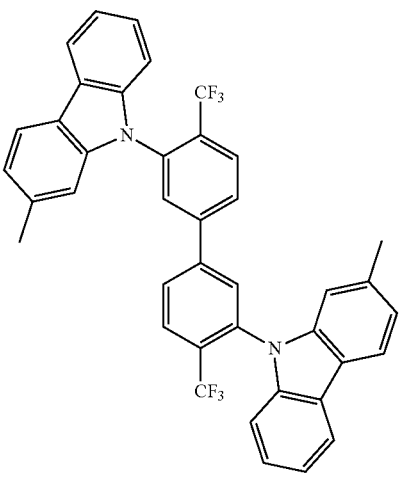

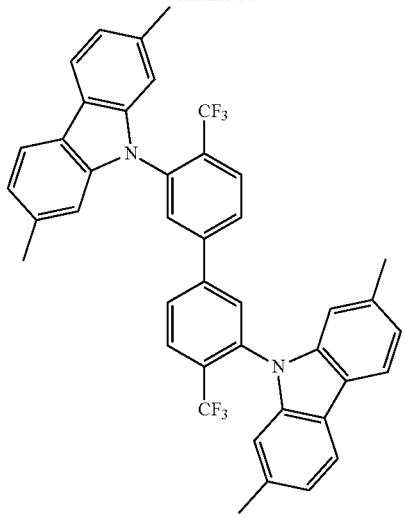
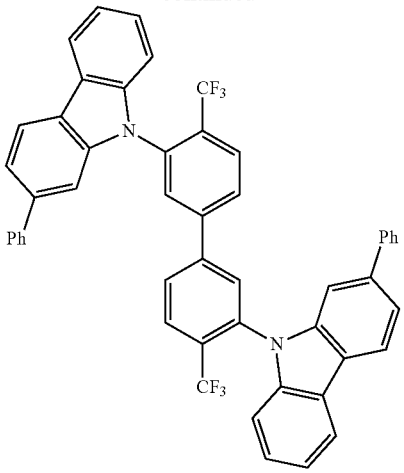
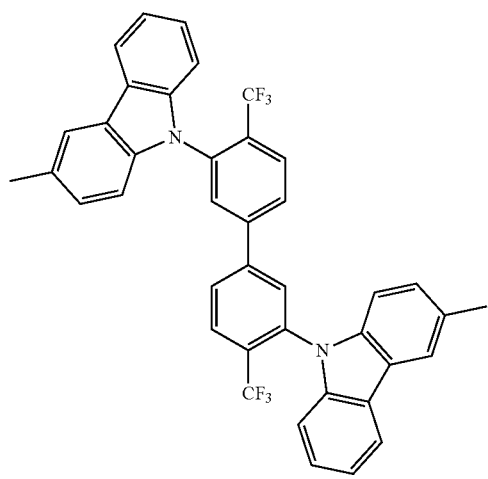
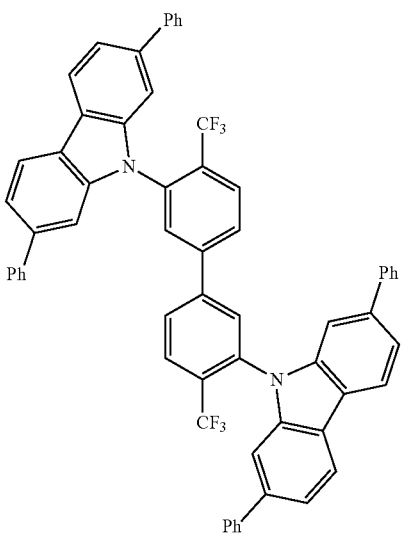
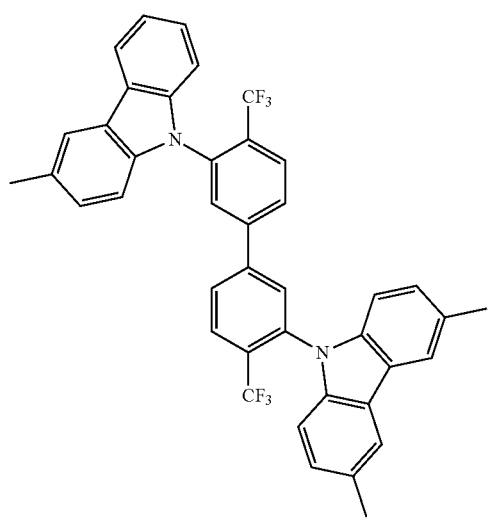
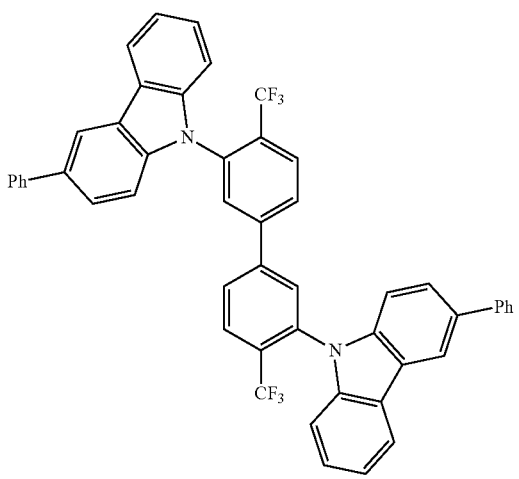

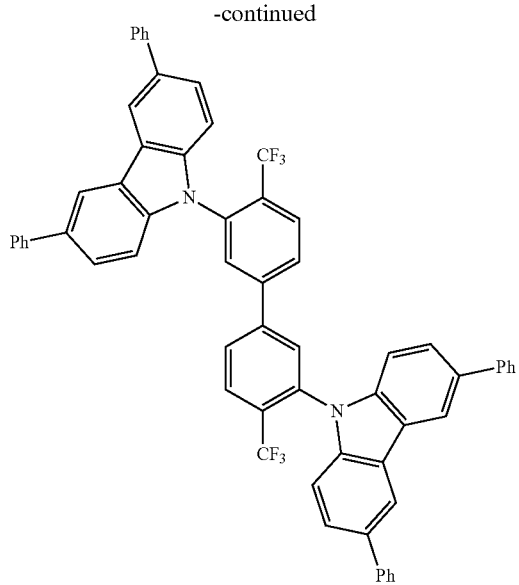
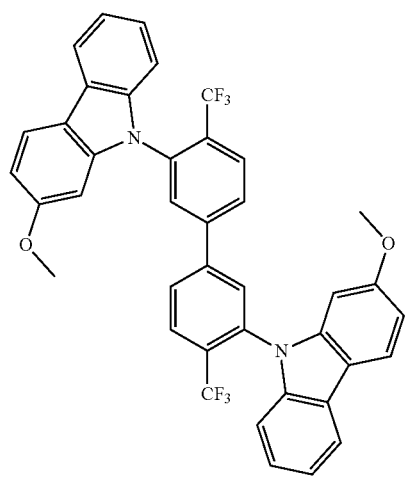
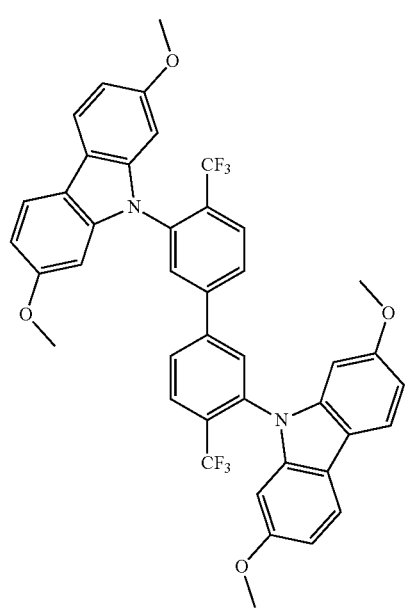
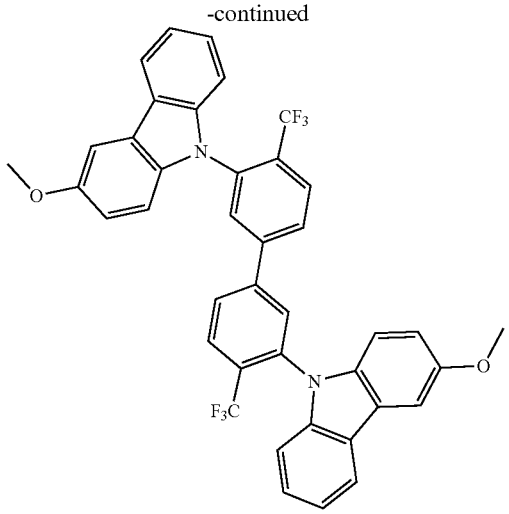
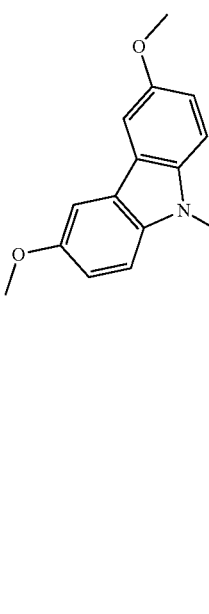
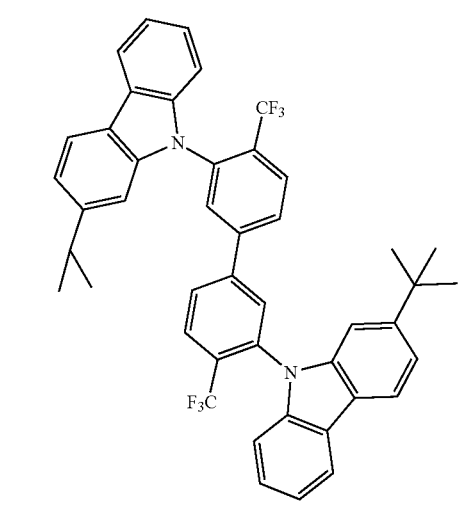

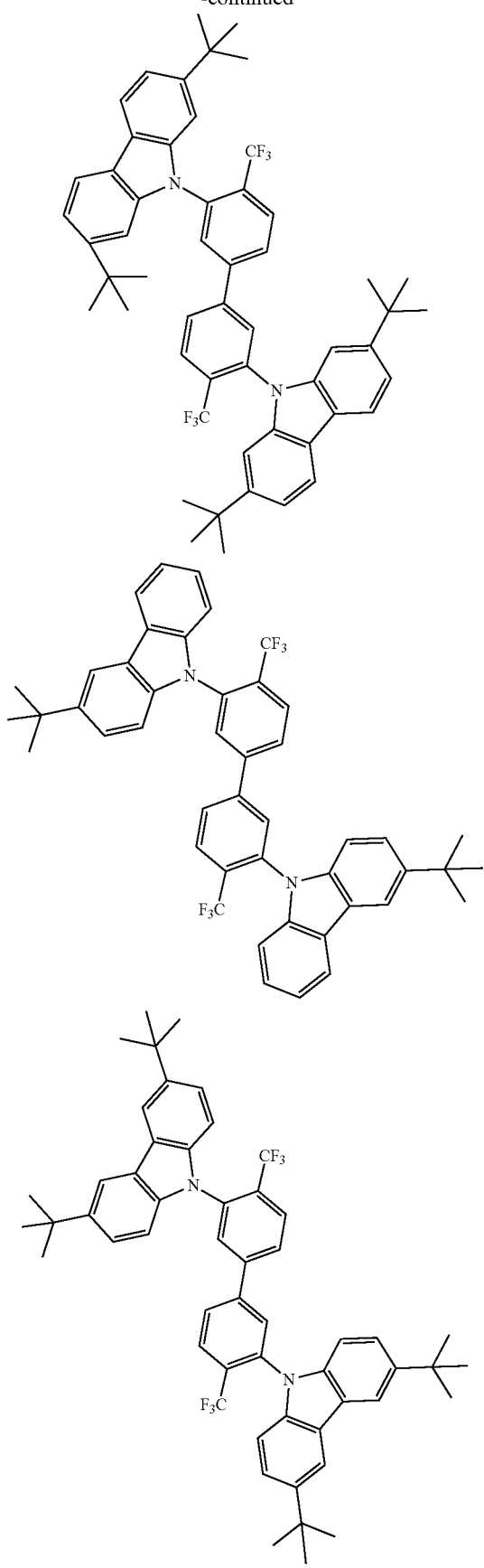
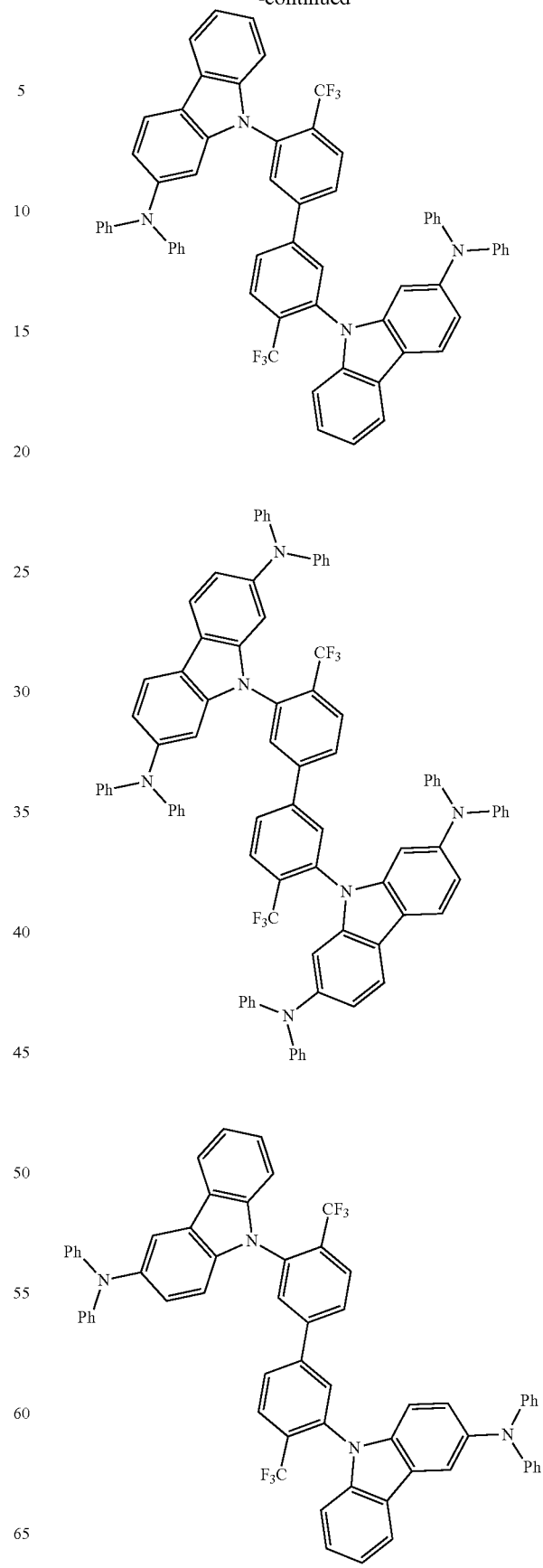

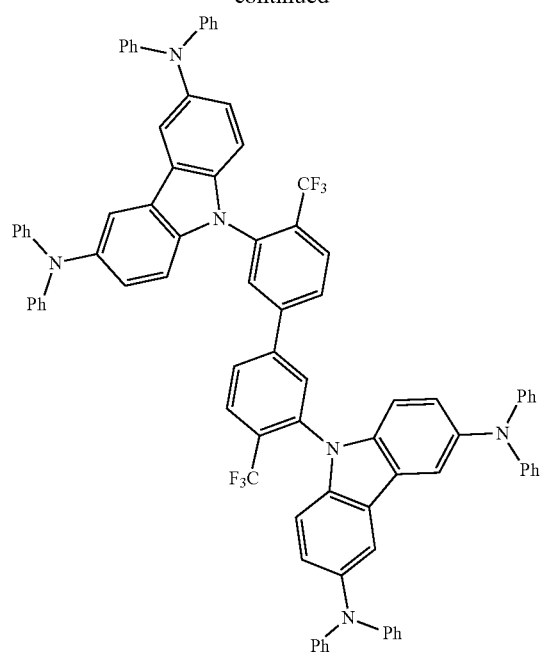
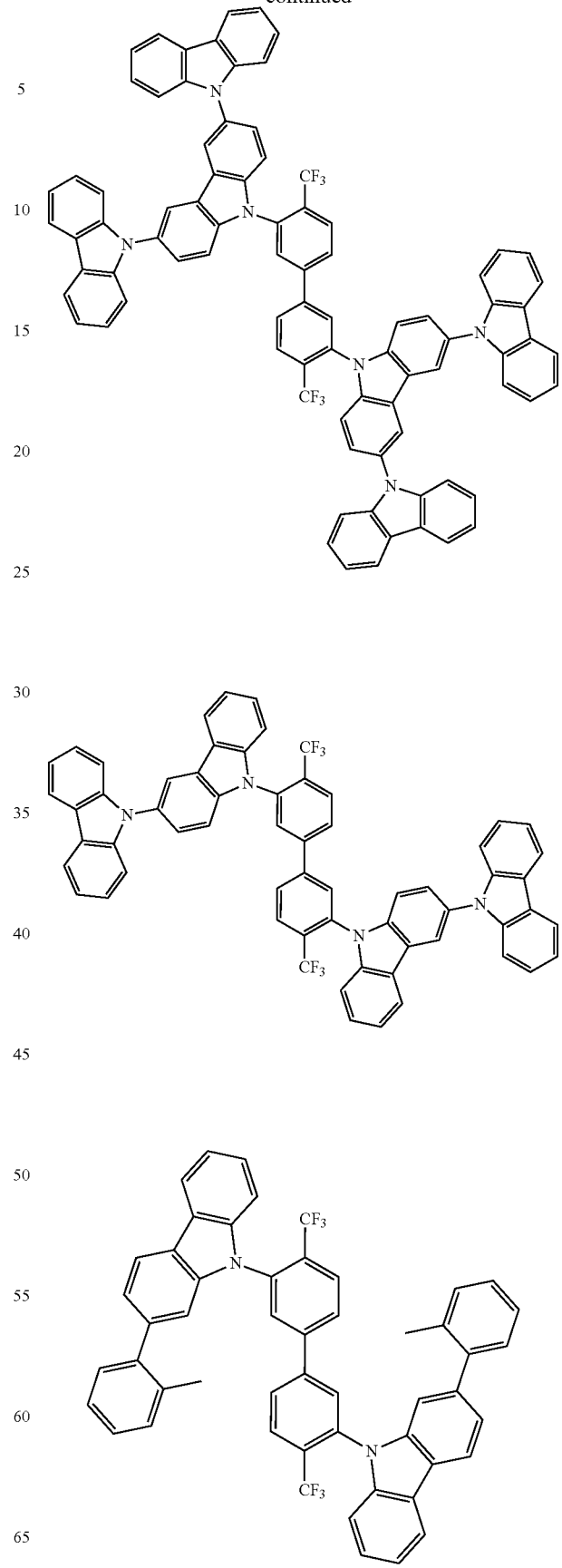

59
-continued
60
-continued
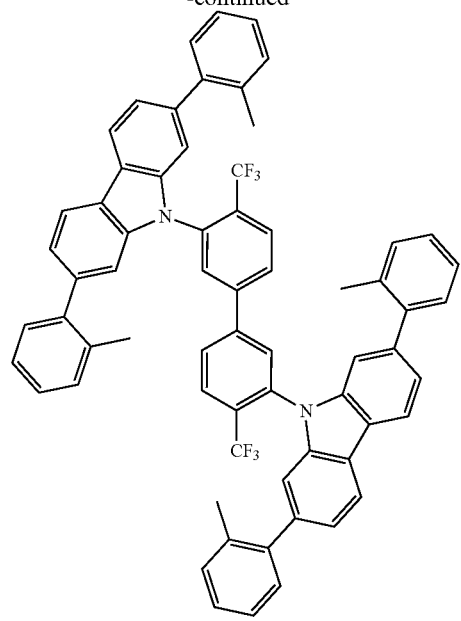
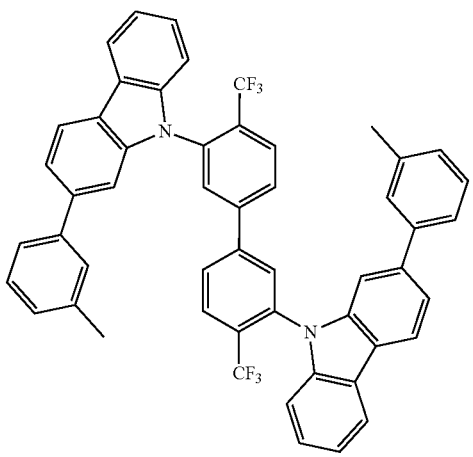
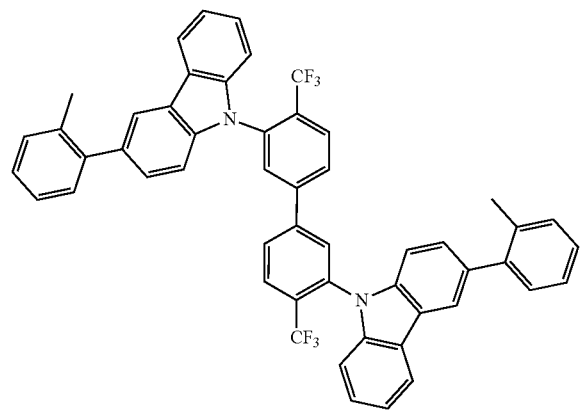
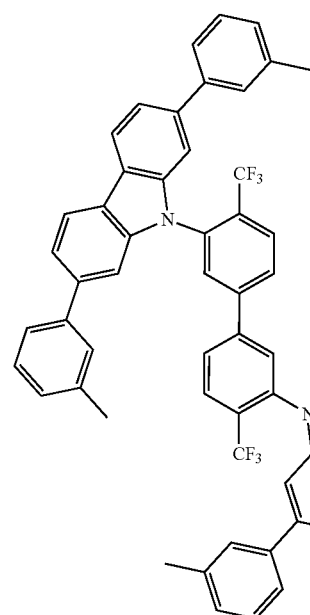
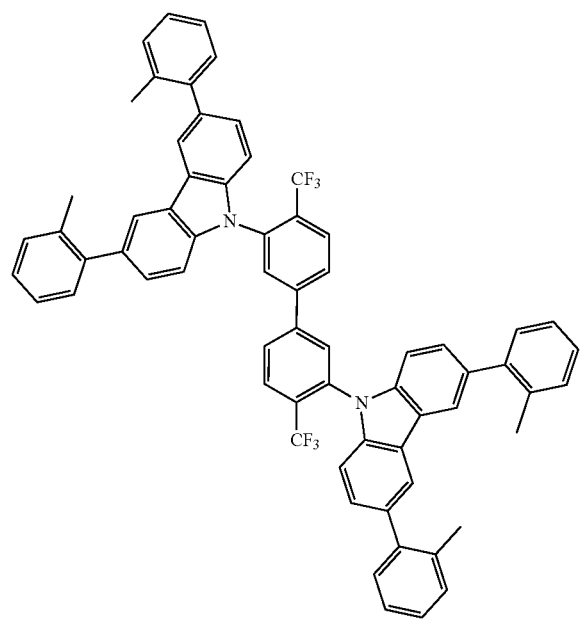
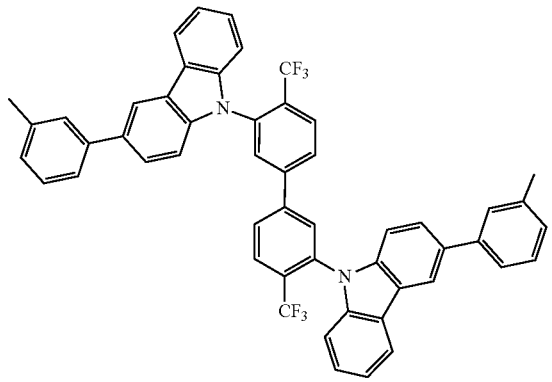

61
-continued
62
-continued
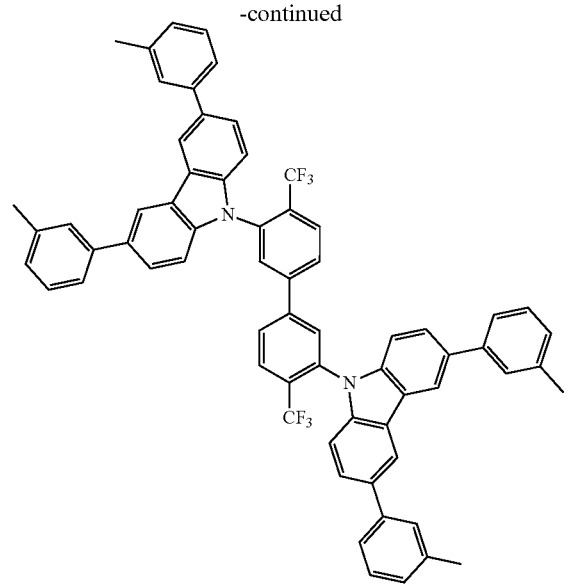
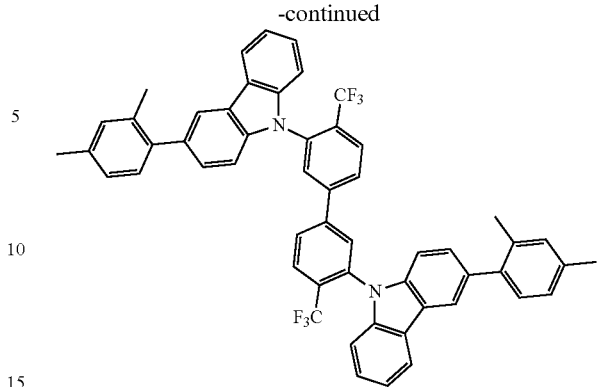
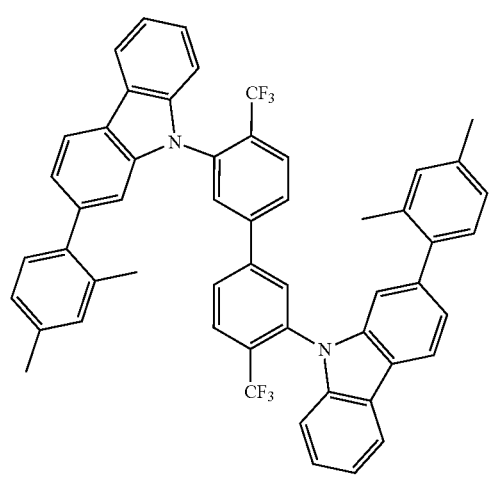
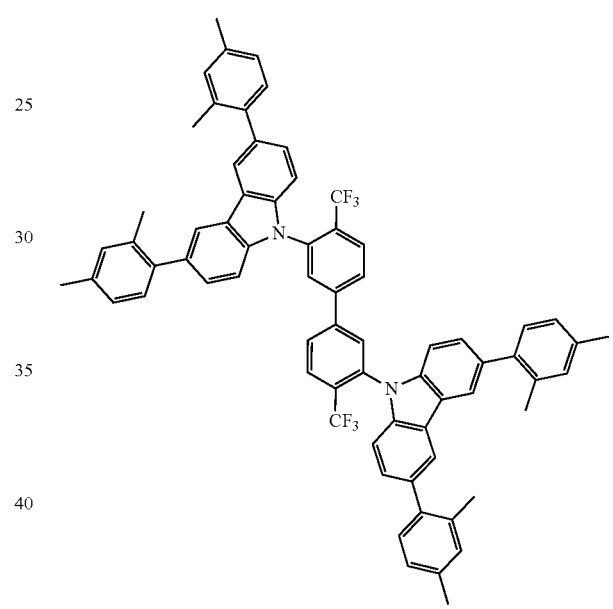
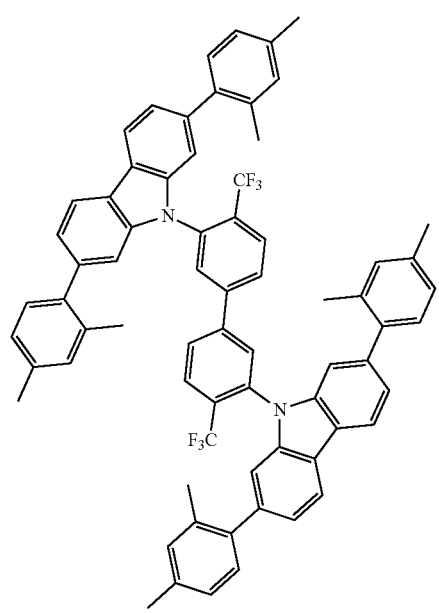
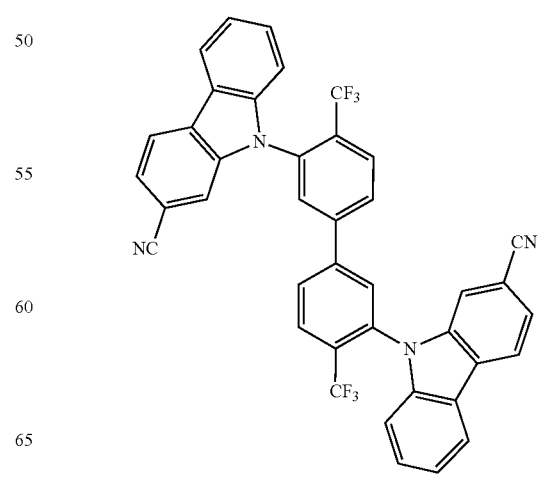

-continued
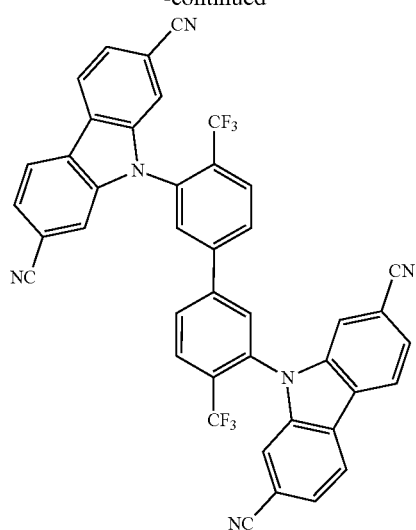
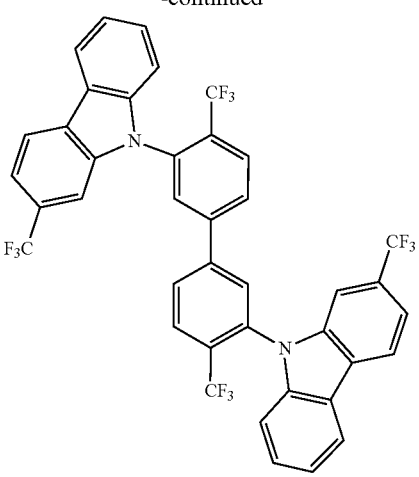
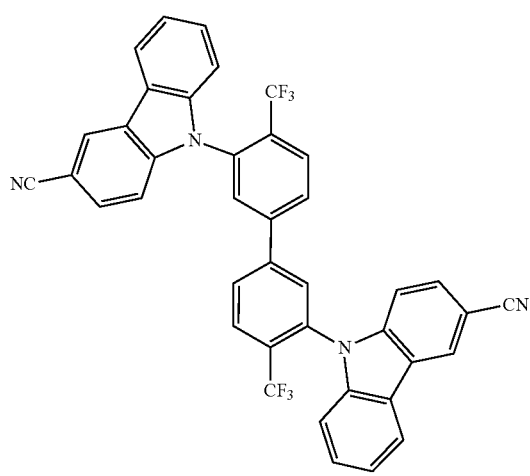
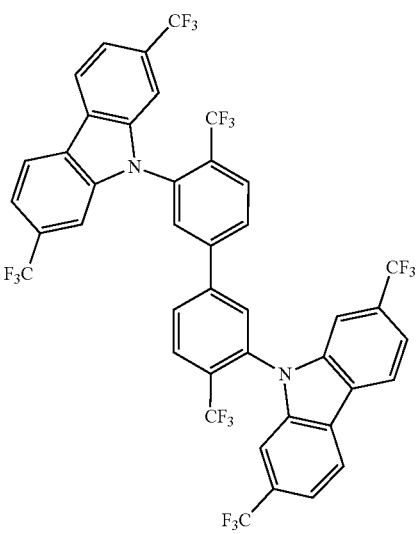
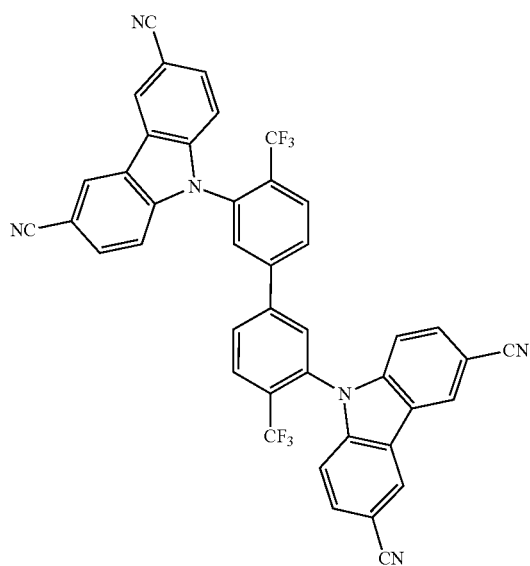
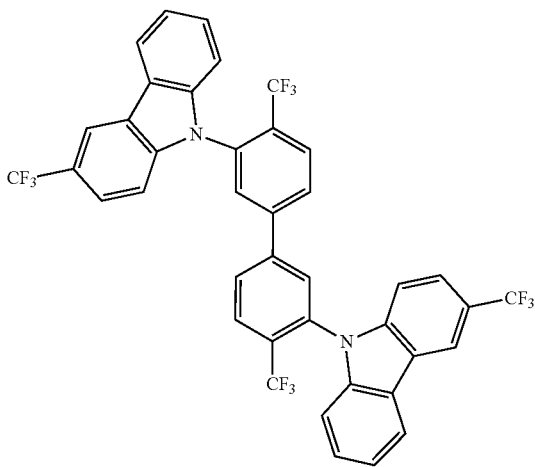

65
-continued
66
-continued
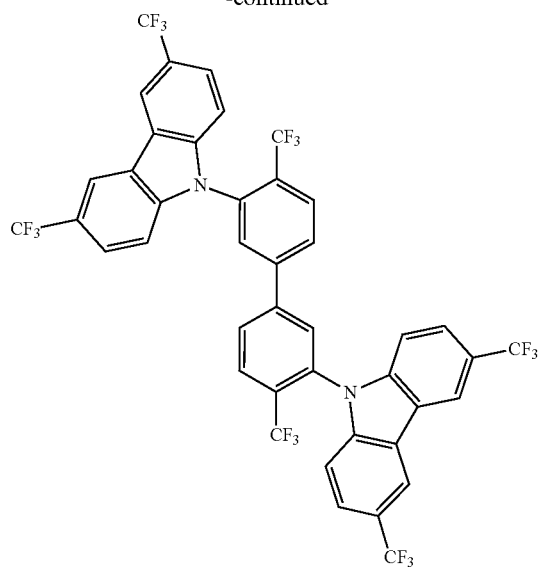
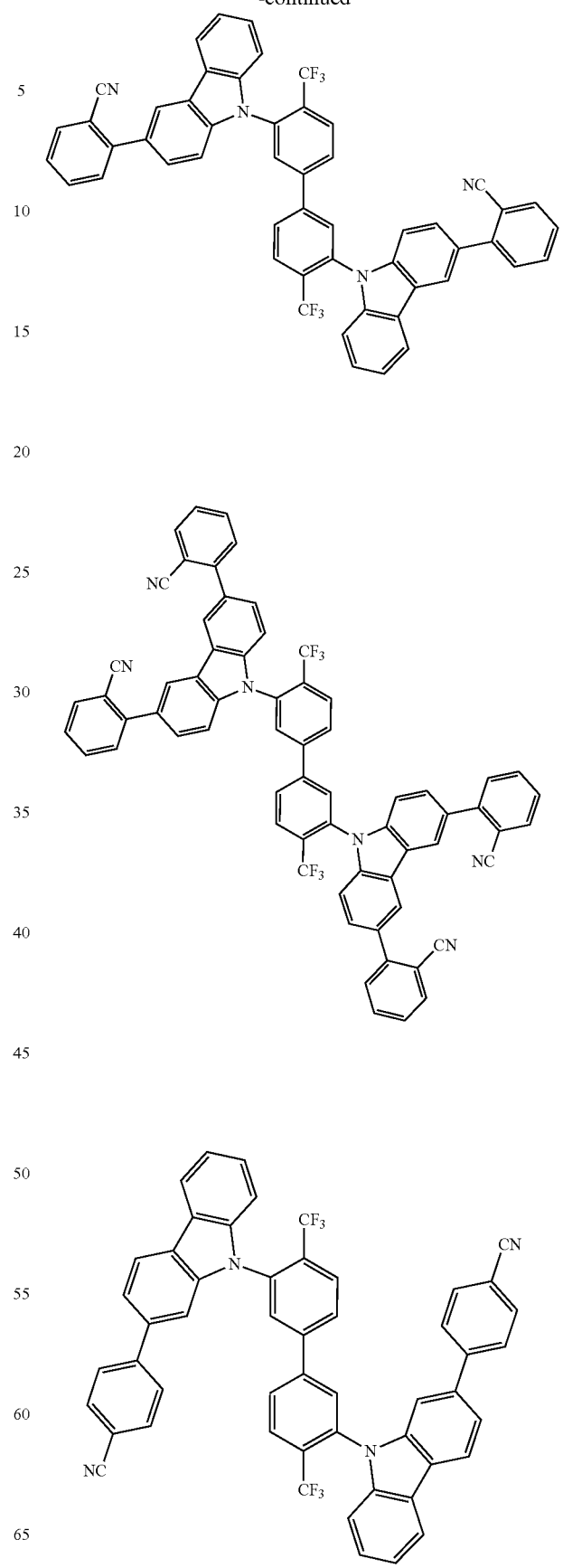

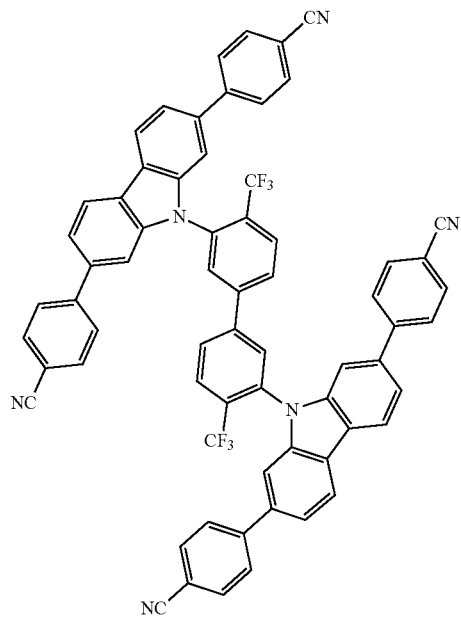
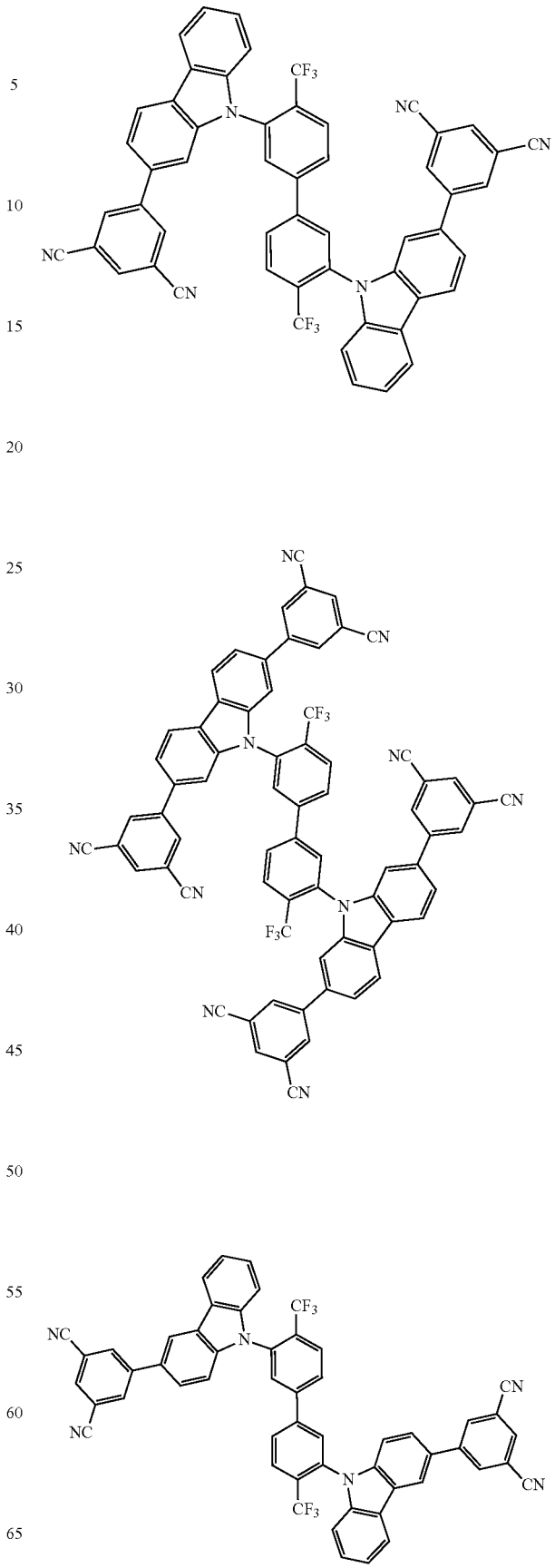

69
-continued
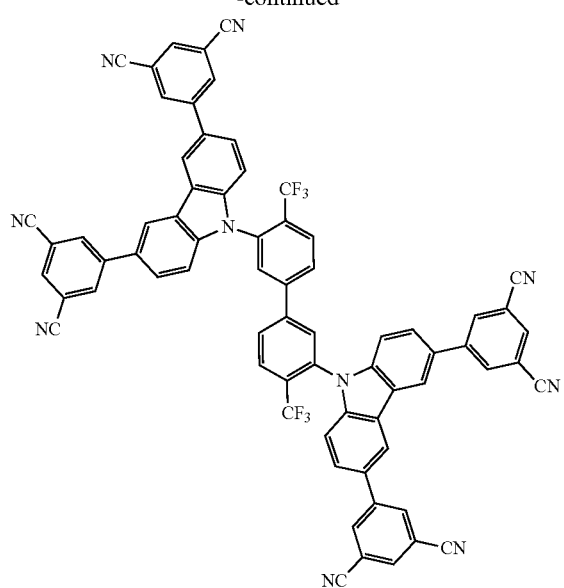
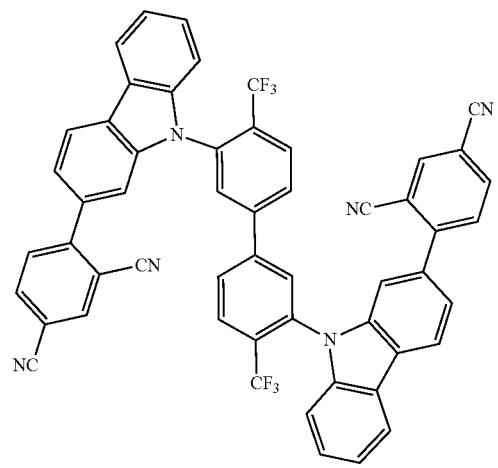
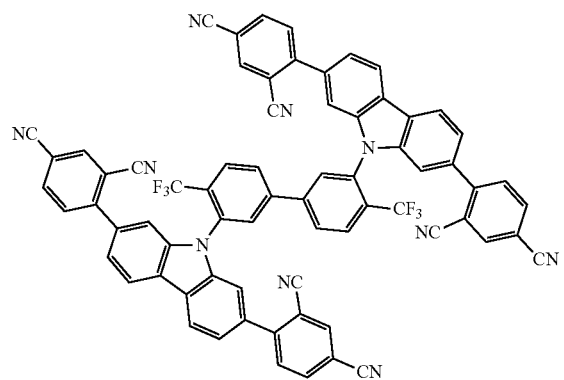
70
-continued
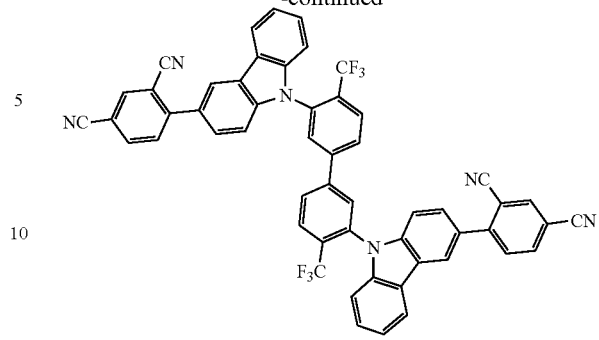
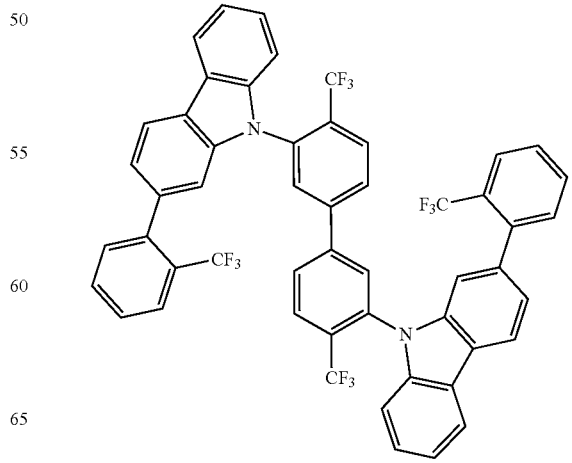

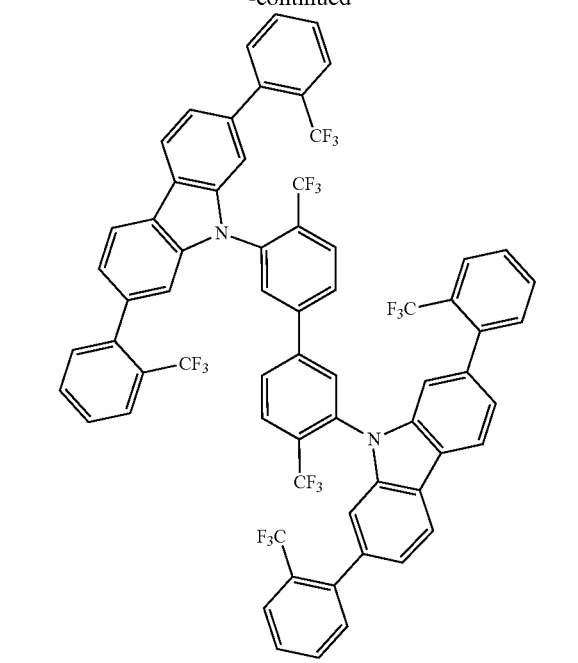
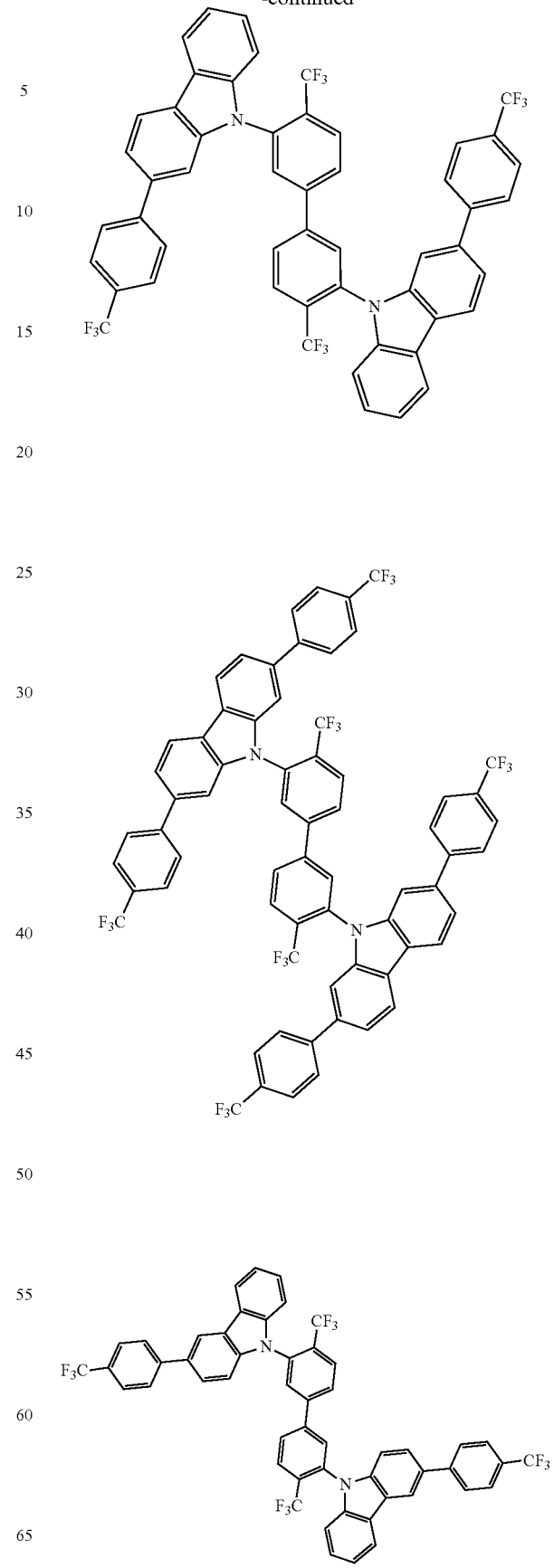

-continued
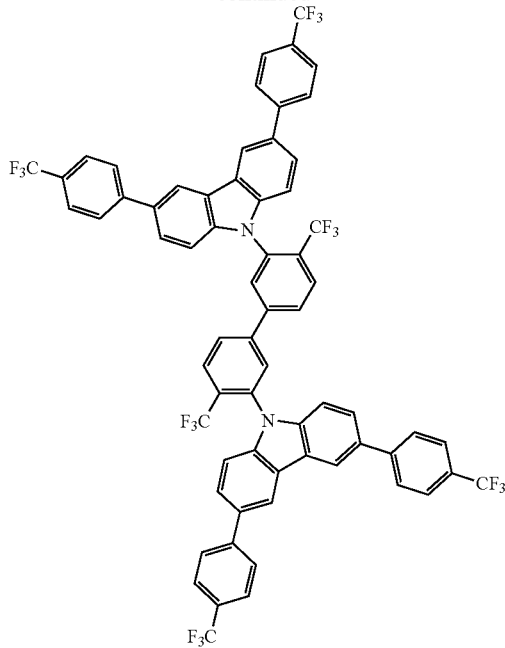
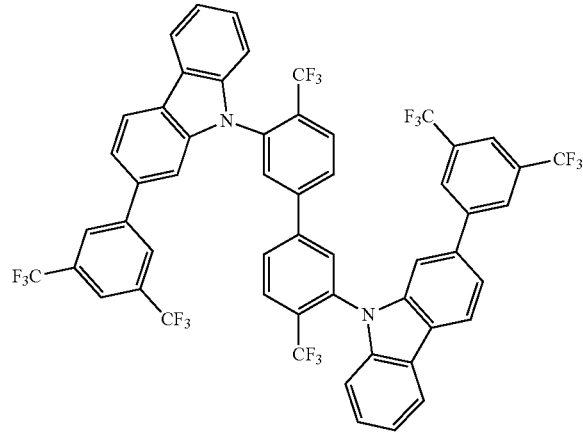
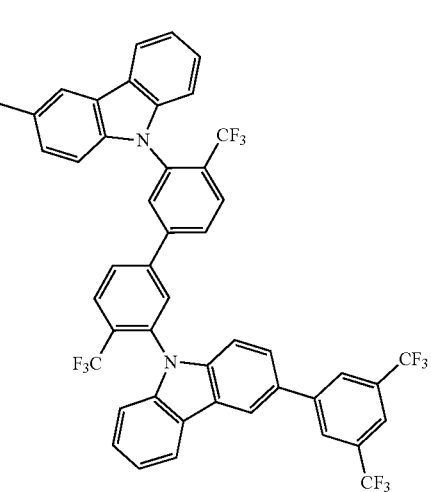

75
-continued

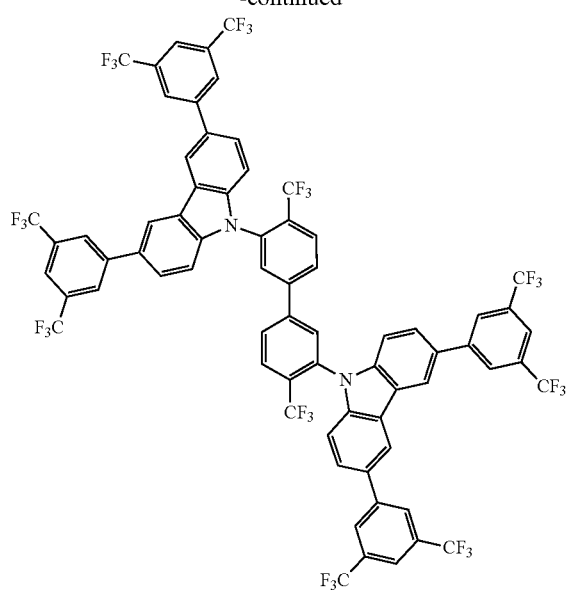

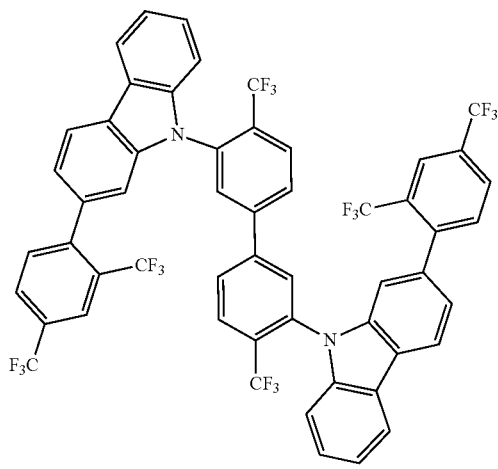

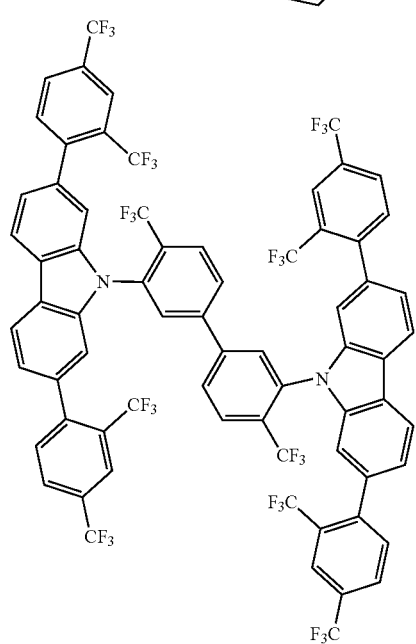

76
-continued

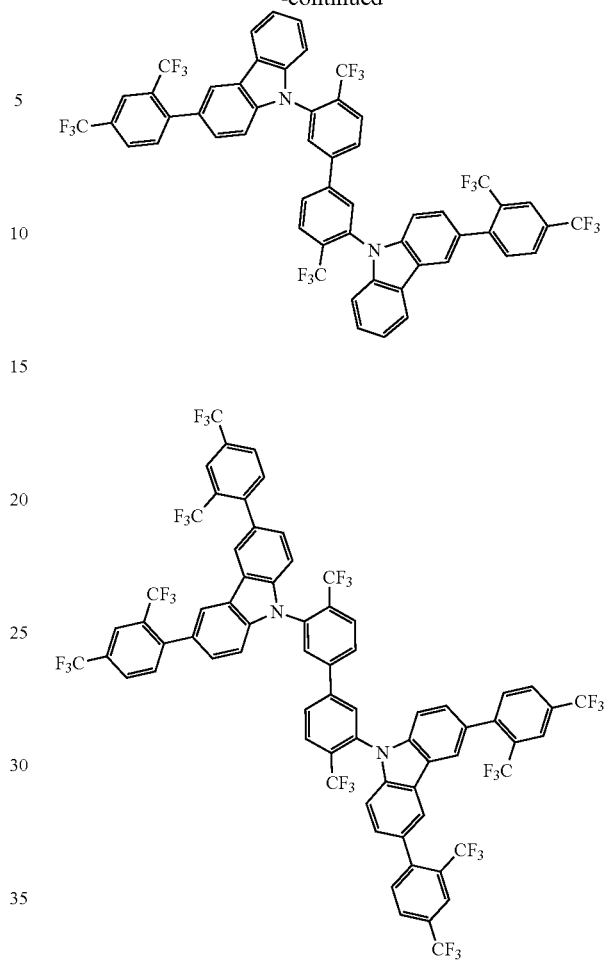

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:

1. An organic molecule, comprising a structure of Formula I,

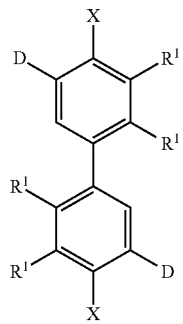

Formula I with

X=CN or CF$_3$, and

D=

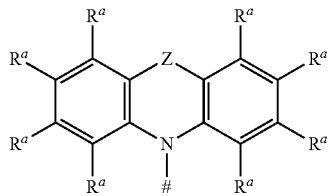

wherein

\# is the point of attachment of unit D to a phenyl ring shown in Formula I;

Z is a direct bond or is selected from the group consisting of CR$^3$R$^4$, C=CR$^3$R$^4$, C=O, C=NR$^3$, NR$^3$, O, SiR$^3$R$^4$, S, S(O), S(O)$_2$;

in each occurrence R$^1$ is the same or different and is selected from the group consisting of:
  H, deuterium;
  a linear alkyl group having 1 to 5 C atoms, wherein one or more H atoms can be replaced by deuterium;
  a linear alkenyl or alkynyl group having 2 to 8 C atoms, wherein one or more H atoms can be replaced by deuterium;
  a branched or cyclic alkyl, alkenyl or alkynyl group having 3 to 10 C atoms, wherein one or more H atoms can be replaced by deuterium; and
  an aromatic ring system having 5 to 15 aromatic ring atoms, which can in each case be substituted with one or more radicals R$^6$;

in each occurrence R$^a$, R$^3$ and R$^4$ is the same or different and is selected from the group consisting of:
  H, deuterium, N(R$^5$)$_2$, OH, Si(R$^5$)$_3$, B(OR$^5$)$_2$, OSO$_2$R$^5$, CF$_3$, CN, F, Br, I;
  a linear alkyl, alkoxy or thioalkoxy group having 1 to 40 C atoms, which can in each case be substituted with one or more radicals R$^5$, wherein one or more non-adjacent CH$_2$ groups can be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and wherein one or more H atoms can be replaced by deuterium, CN, CF$_3$ or NO$_2$;
  a linear alkenyl or alkynyl group having 2 to 40 C atoms, which can in each case be substituted with one or more radicals R$^5$, wherein one or more non-adjacent CH$_2$ groups can be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and wherein one or more H atoms can be replaced by deuterium, CN, CF$_3$ or NO$_2$;
  a branched or cyclic alkyl, alkenyl, alkynyl, alkoxy or thioalkoxy group having 3 to 40 C atoms, which can in each case be substituted with one or more radicals R$^5$, wherein one or more non-adjacent CH$_2$ groups can be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and wherein one or more H atoms can be replaced by deuterium, CN, CF$_3$ or NO$_2$;
  an aromatic ring system having 5 to 60 aromatic ring atoms, which can in each case be substituted with one or more radicals R$^5$;
  an aryloxy or heteroaryloxy group having 5 to 60 aromatic ring atoms, which can be substituted with one or more radicals R$^5$; and
  a diarylamino group, diheteroarylamino group or arylheteroarylamino group having 10 to 40 aromatic ring atoms, which can be substituted with one or more radicals R$^5$;

in each occurrence R$^5$ is the same or different and is selected from the group consisting of:
  H, deuterium, N(R$^6$)$_2$, OH, Si(R$^6$)$_3$, B(OR$^6$)$_2$, OSO$_2$R$^6$, CF$_3$, CN, F, Br, I;
  a linear alkyl, alkoxy or thioalkoxy group having 1 to 40 C atoms, which can in each case be substituted with one or more radicals R$^6$, wherein one or more non-adjacent CH$_2$ groups can be replaced by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$ and wherein one or more H atoms can be replaced by deuterium, CN, CF$_3$ or NO$_2$;
  a linear alkenyl or alkynyl group having 2 to 40 C atoms, which can in each case be substituted with one or more radicals R$^6$, wherein one or more non-adjacent CH$_2$ groups can be replaced by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$ and wherein one or more H atoms can be replaced by deuterium, CN, CF$_3$ or NO$_2$;
  a branched or cyclic alkyl, alkenyl, alkynyl, alkoxy or thioalkoxy group having 3 to 40 C atoms, which can in each case be substituted with one or more radicals R$^6$, wherein one or more non-adjacent CH$_2$ groups can be replaced by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$ and wherein one or more H atoms can be replaced by deuterium, CN, CF$_3$ or NO$_2$;
  an aromatic or heteroaromatic ring system having 5 to 60 aromatic ring atoms, which can in each case be substituted with one or more radicals R$^6$;
  an aryloxy or heteroaryloxy group having 5 to 60 aromatic ring atoms, which can be substituted with one or more radicals R$^6$; and
  a diarylamino group, diheteroarylamino group or arylheteroarylamino group having 10 to 40 aromatic ring atoms, which can be substituted with one or more radicals R$^6$;

in each occurrence R$^6$ is the same or different and is selected from the group consisting of:
  H, deuterium, OH, CF$_3$, CN, F, Br, I;
  a linear alkyl, alkoxy or thioalkoxy group having 1 to 5 C atoms, wherein one or more H atoms can be replaced by deuterium, CN, CF$_3$ or NO$_2$;
  a linear alkenyl or alkynyl group having 2 to 5 C atoms, wherein one or more H atoms can be replaced by deuterium, CN, CF$_3$ or NO$_2$;
  a branched or cyclic alkyl, alkenyl, alkynyl, alkoxy or thioalkoxy group having 3 to 5 C atoms, wherein one or more H atoms can be replaced by deuterium, CN, CF$_3$ or NO$_2$;
  an aromatic or heteroaromatic ring system having 5 to 60 aromatic ring atoms;
  an aryloxy or heteroaryloxy group having 5 to 60 aromatic ring atoms; and
  a diarylamino group, diheteroarylamino group or arylheteroarylamino group having 10 to 40 aromatic ring atoms;

wherein each of the radicals $R^a$, $R^3$, $R^4$ or $R^5$ can also form a mono- or polycyclic, aliphatic, aromatic and/or benzoannelated ring system with one or more further radicals $R^a$, $R^3$, $R^4$ or $R^5$;

wherein the two D groups are identical; and wherein at least one $R^a$ is not H.

2. The organic molecule according to claim 1, wherein $R^1$ is H or methyl.

3. The organic molecule according to claim 1, wherein both X are CN.

4. The organic molecule according to claim 1, wherein D comprises a structure of Formula IIa:

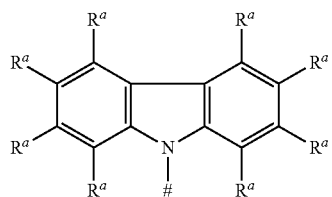

Formula IIa wherein # and $R^a$ have the aforestated meanings.

5. The organic molecule according to claim 1, wherein D comprises a structure of Formula IIb:

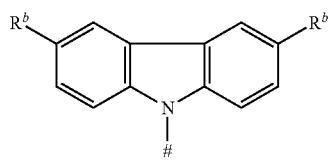

Formula IIb wherein
in each occurrence $R^b$ is the same or different and is selected from the group consisting of:
$N(R^5)_2$, OH, $Si(R^5)_3$, $B(OR^5)_2$, $OSO_2R^5$, $CF_3$, CN, F, Br, I;
a linear alkyl, alkoxy or thioalkoxy group having 1 to 40 C atoms, which can in each case be substituted with one or more radicals $R^5$, wherein one or more non-adjacent $CH_2$ groups can be replaced by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$ and wherein one or more H atoms can be replaced by deuterium, CN, $CF_3$ or $NO_2$;
a linear alkenyl or alkynyl group having 2 to 40 C atoms, which can in each case be substituted with one or more radicals $R^5$, wherein one or more non-adjacent $CH_2$ groups can be replaced by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$ and wherein one or more H atoms can be replaced by deuterium, CN, $CF_3$ or $NO_2$;
a branched or cyclic alkyl, alkenyl, alkynyl, alkoxy or thioalkoxy group having 3 to 40 C atoms, which can in each case be substituted with one or more radicals $R^5$, wherein one or more non-adjacent $CH_2$ groups can be replaced by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$ and wherein one or more H atoms can be replaced by deuterium, CN, $CF_3$ or $NO_2$;
an aromatic or heteroaromatic ring system having 5 to 60 aromatic ring atoms, which in each case can be substituted with one or more radicals $R^5$;
an aryloxy or heteroaryloxy group having 5 to 60 aromatic ring atoms, which can be substituted with one or more radicals $R^5$; and
a diarylamino group, diheteroarylamino group or aryl-heteroarylamino group having 10 to 40 aromatic ring atoms, which can be substituted with one or more radicals $R^5$;
and # and $R^5$ have the aforestated meanings.

6. The organic molecule according to claim 1, wherein D comprises a structure of Formula IIc:

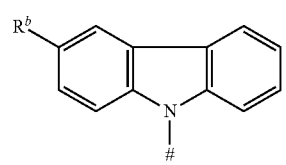

Formula IIc wherein
in each occurrence $R^b$ is the same or different and is selected from the group consisting of:
$N(R^5)_2$, OH, $Si(R^5)_3$, $B(OR^5)_2$, $OSO_2R^5$, $CF_3$, CN, F, Br, I;
a linear alkyl, alkoxy or thioalkoxy group having 1 to 40 C atoms, which can in each case be substituted with one or more radicals $R^5$, wherein one or more non-adjacent $CH_2$ groups can be replaced by $R^5C{=}CR^5$, $Si(R^5)_2$, $C{\equiv}C$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$ and wherein one or more H atoms can be replaced by deuterium, CN, $CF_3$ or $NO_2$;
a linear alkenyl or alkynyl group having 2 to 40 C atoms, which can in each case be substituted with one or more radicals $R^5$, wherein one or more non-adjacent $CH_2$ groups can be replaced by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$ and wherein one or more H atoms can be replaced by deuterium, CN, $CF_3$ or $NO_2$;
a branched or cyclic alkyl, alkenyl, alkynyl, alkoxy or thioalkoxy group having 3 to 40 C atoms, which can in each case be substituted with one or more radicals $R^5$, wherein one or more non-adjacent $CH_2$ groups can be replaced by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$ and wherein one or more H atoms can be replaced by deuterium, CN, $CF_3$ or $NO_2$;
an aromatic or heteroaromatic ring system having 5 to 60 aromatic ring atoms, which in each case can be substituted with one or more radicals $R^5$;
an aryloxy or heteroaryloxy group having 5 to 60 aromatic ring atoms, which can be substituted with one or more radicals $R^5$; and
a diarylamino group, diheteroarylamino group or aryl-heteroarylamino group having 10 to 40 aromatic ring atoms, which can be substituted with one or more radicals $R^5$;
and # and $R^5$ have the aforestated meanings.

7. The organic molecule according to claim 5, wherein in each occurrence $R^b$ is the same or different and is selected from the group consisting of:

Me, $^i$Pr, $^t$Bu, CN, CF$_3$;

Ph, which can in each case be substituted with one or more radicals selected from Me, $^i$Pr, $^t$Bu, CN, CF$_3$, and Ph;

pyridinyl, which can in each case be substituted with one or more radicals selected from Me, $^i$Pr, $^t$Bu, CN, CF$_3$, and Ph;

pyrimidinyl which can in each case be substituted with one or more radicals selected from Me, $^i$Pr, $^t$Bu, CN, CF$_3$, and Ph;

carbazolyl which can in each case substituted with one or more radicals selected from Me, $^i$Pr, $^t$Bu, CN, CF$_3$, and Ph; and N(Ph)$_2$.

8. An optoelectronic device comprising an organic molecule according to claim 1.

9. The optoelectronic device according to claim 8, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

10. A composition comprising:
    (a) at least one organic molecule according to claim 1 as a luminescent emitter and/or a host material; and
    (b) one or more luminescent emitters and/or host materials different from the at least one organic molecule according to claim 1.

11. An optoelectronic device comprising the composition according to claim 10.

12. The optoelectronic device according to claim 11, comprising:
    a substrate;
    an anode; and
    a cathode, wherein the anode or the cathode is disposed on the substrate; and
    at least one light-emitting layer disposed between the anode and the cathode and which comprises the composition according to claim 10.

13. The optoelectronic device according to claim 8, wherein the organic molecule is one of a luminescent emitter and a host material in an optoelectronic component.

14. The optoelectronic device according to claim 9, wherein the organic molecule is one of a luminescent emitter and a host material in an optoelectronic component.

15. The optoelectronic device according to claim 13, wherein the proportion of the organic molecule in the luminescent emitter or the host material is in the range of 1% to 80%.

16. The optoelectronic device according to claim 8, comprising
    a substrate;
    an anode;
    a cathode, wherein the anode or the cathode is disposed on the substrate; and
    at least one light-emitting layer disposed between the anode and the cathode and which comprises the organic molecule.

17. The organic molecule according to claim 2, wherein both X are CN.

18. The organic molecule according to claim 6, wherein in each occurrence $R^b$ is the same or different and is selected from the group consisting of:
    Me, $^i$Pr, $^t$Bu, CN, CF$_3$;
    Ph, which can in each case be substituted with one or more radicals selected from Me, $^i$Pr, $^t$Bu, CN, CF$_3$, and Ph;
    pyridinyl, which can in each case be substituted with one or more radicals selected from Me, $^i$Pr, $^t$Bu, CN, CF$_3$, and Ph;
    pyrimidinyl which can in each case be substituted with one or more radicals selected from Me, $^i$Pr, $^t$Bu, CN, CF$_3$, and Ph;
    carbazolyl which can in each case substituted with one or more radicals selected from Me, $^i$Pr, $^t$Bu, CN, CF$_3$, and Ph; and
    N(Ph)$_2$.

19. A process for producing an optoelectronic component, comprising processing of the organic molecule according to claim 1 by a vacuum vaporization process or from a solution.

20. The organic molecule according to claim 1, wherein $R^1$ is an aromatic ring system having 6 to 15 aromatic hydrocarbon group ring atoms.

* * * * *